United States Patent [19]

Gielisse

[11] 4,394,580
[45] Jul. 19, 1983

[54] METHOD AND APPARATUS FOR ANALYZING GEMS

[75] Inventor: Peter J. Gielisse, Brewster, Minn.

[73] Assignee: L.C.E. Ltd., Worthington, Minn.

[21] Appl. No.: 287,165

[22] Filed: Jul. 27, 1981

[51] Int. Cl.³ ............................................ G01N 21/64
[52] U.S. Cl. .................................................. 250/461.1
[58] Field of Search .............. 250/461 R, 272; 356/30

[56] References Cited

U.S. PATENT DOCUMENTS

| | | | |
|---|---|---|---|
| 3,903,422 | 9/1975 | Buhrer | 250/461 R |
| 3,950,102 | 4/1976 | Eickhorst | 356/30 X |
| 4,012,141 | 3/1977 | Hanneman | 356/30 |
| 4,037,961 | 7/1977 | Macemom | 250/461 R X |
| 4,117,338 | 9/1978 | Adrion et al. | 250/461 R |
| 4,125,770 | 11/1978 | Lang | 250/272 |
| 4,291,230 | 9/1981 | Heiss | 250/461 R X |

Primary Examiner—Davis L. Willis
Attorney, Agent, or Firm—Merchant, Gould, Smith, Edell, Welter & Schmidt

[57] ABSTRACT

The disclosure is directed to an apparatus and method for analyzing gem specimens. In the disclosed embodiment, a small cabinet includes a source discharge lamp for radiating electromagnetic energy over a broad spectrum of wavelengths. A gem specimen is placed in a small drawer that, upon closure, becomes an optically sealed chamber in communication with the radiation source. Also upon closure, a mechanical shutter mechanism permits registration between the radiation source, gem specimen and a photocell detector that senses radiation emitted from the gem specimen as a result of its interaction with the spectrum of wavelengths from the radiation source. This interaction comprises the combined processes of transmission of and absorption by the gem specimen of the source radiation, internal reflection and internal excitation (e.g., fluorescence), the latter of which produces a frequency shift to a narrow spectrum of energy which the photocell detector is specifically designed to sense. The output of the photocell detector is an analog signal that is processed by electronic circuitry in one of two manners. First, the signal is digitized through an analog to digital converter and is displayed as a numerical digital readout. In the second manner, the analog signal is compared with one or more groups of reference values corresponding to different species of gems. If the analog signal falls within a first arbitrary range of values, it is determined to be "natural". In a second arbitrary range, it is determined to be "synthetic". A third range falls between the first and second ranges, and a value within this range is indicative of a gem of indeterminate origin or an operational malfunction. Another group of reference values is used to determine either of two abnormal conditions; viz., a blockage of radiated energy to the detector or the absence of a gem from the specimen holder. The apparatus readout comprises a liquid crystal display that selectively indicates the mode of operation, the natural, synthetic or indeterminate nature of the gem specimen, and a digital readout of a unitless, arbitrary number which may be used to determine gem quality.

46 Claims, 23 Drawing Figures

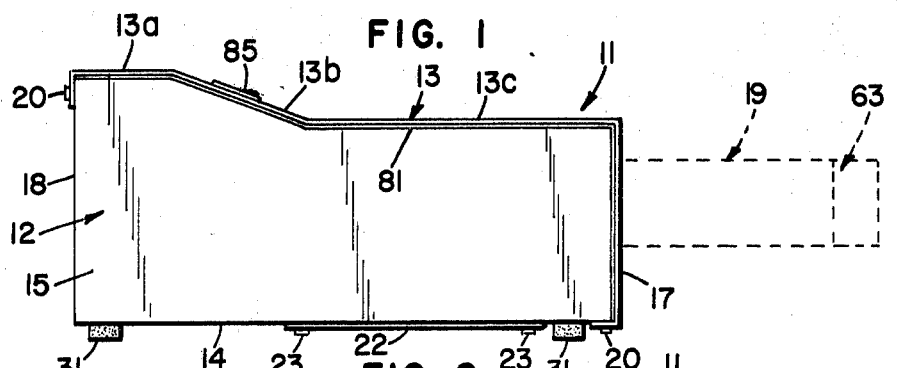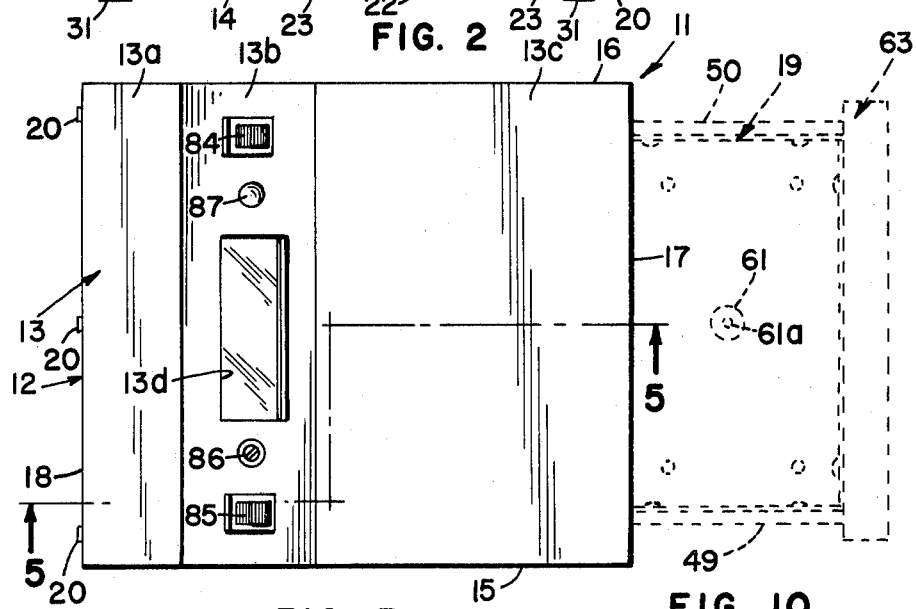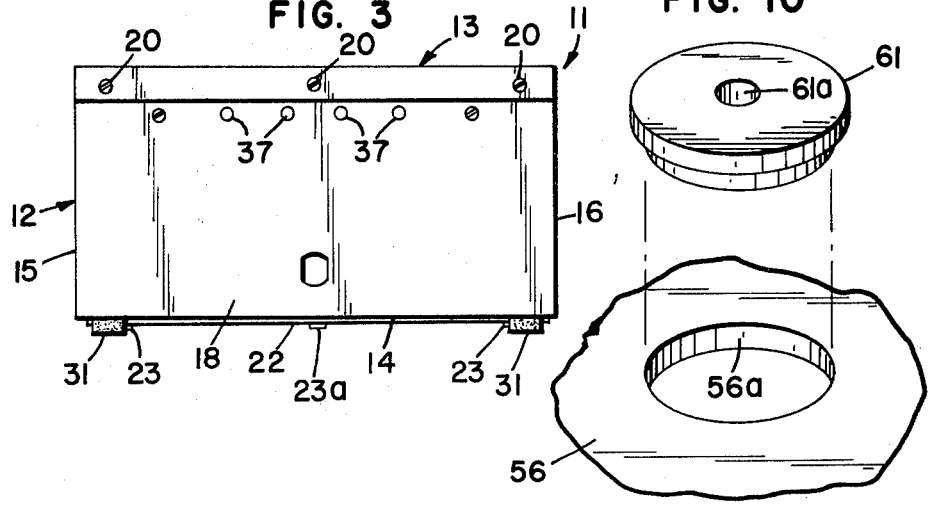

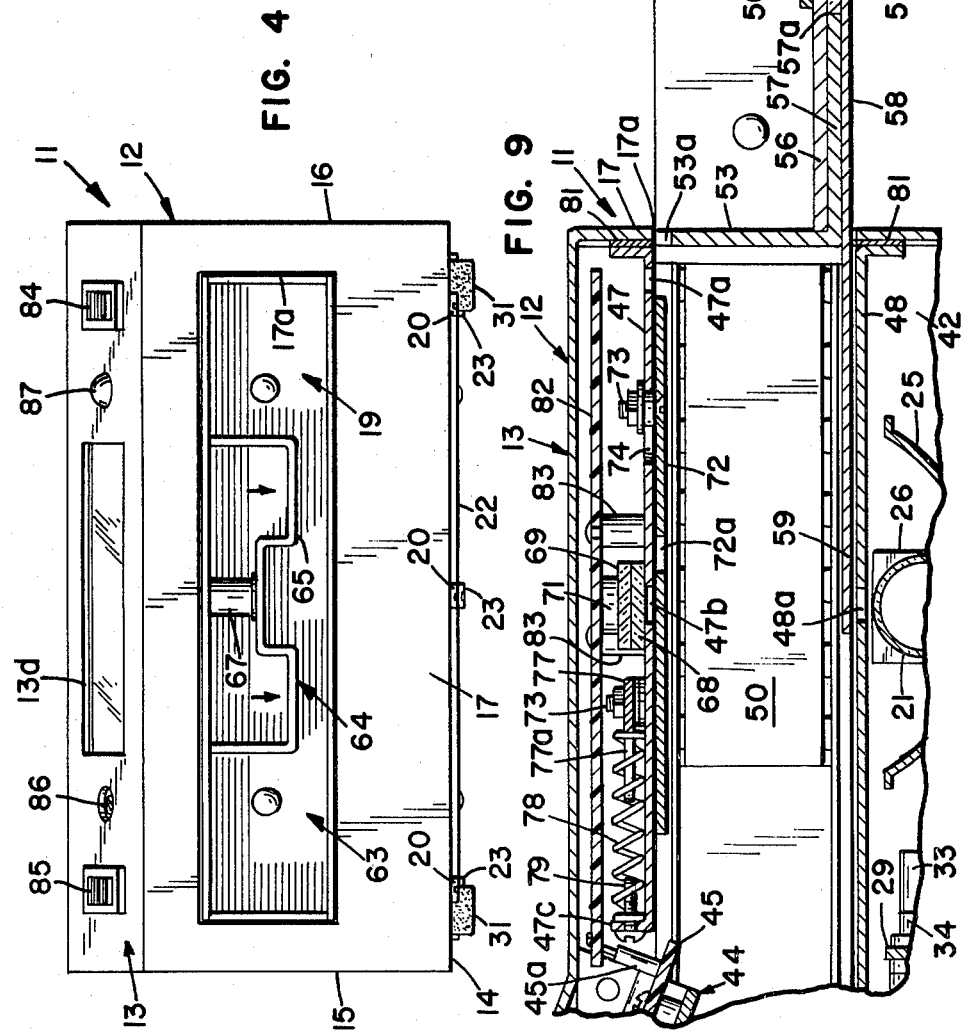

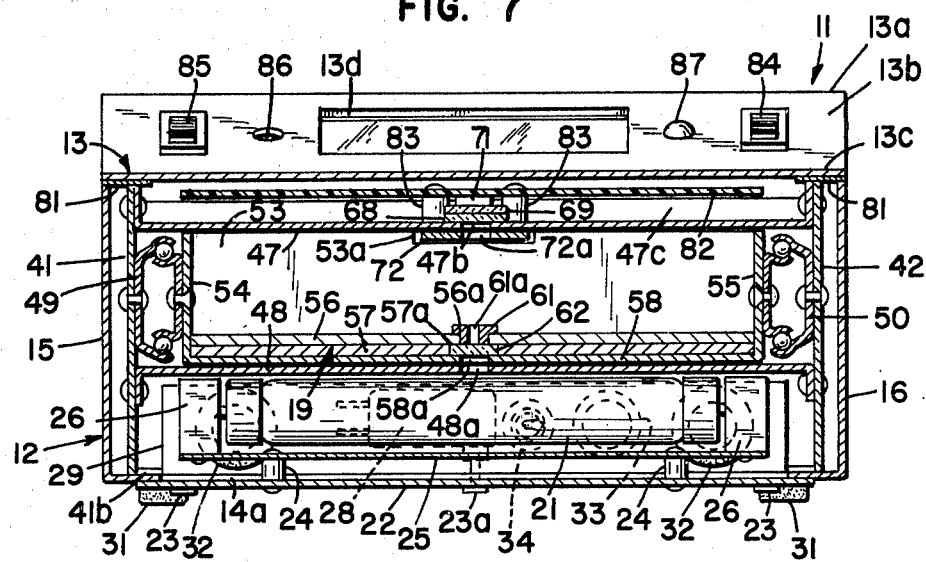
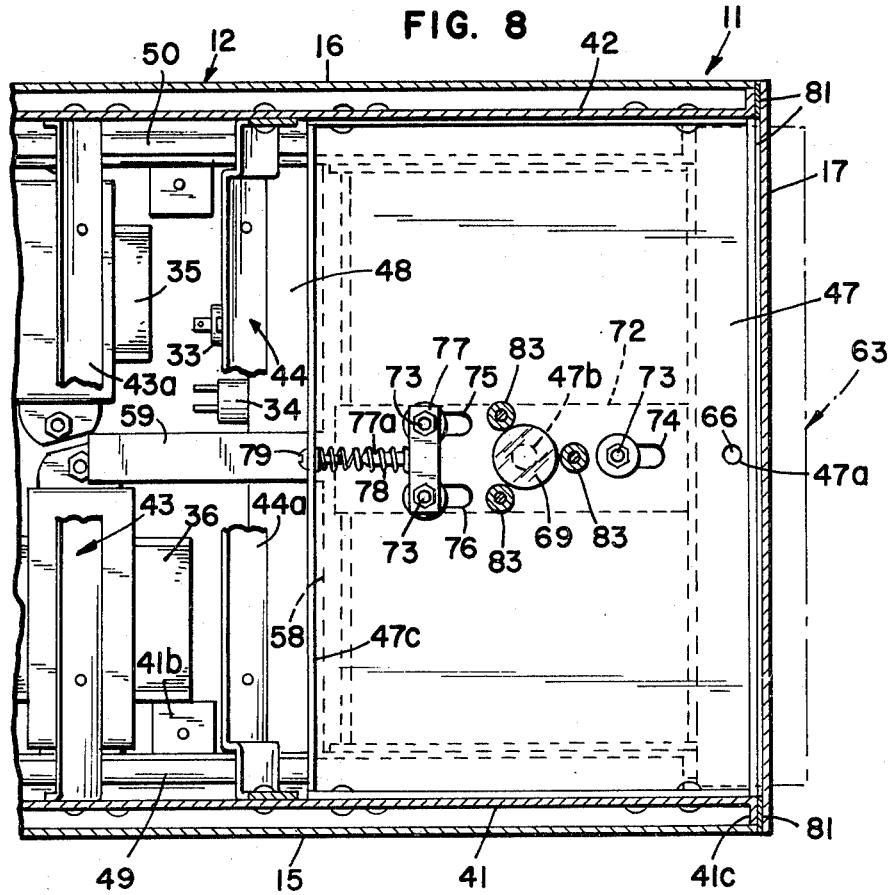

METHOD AND APPARATUS FOR ANALYZING GEMS

TECHNICAL FIELD

The invention relates generally to apparatus for analyzing gems and is specifically directed to a digital gem analyzer capable of distinguishing between natural and synthetic gems as well as quantitatively analyzing gems within a particular origin group.

BACKGROUND OF THE INVENTION

A variety of processes have been perfected which allow the synthesis of crystalline specimens in the laboratory which, with reference to their mode of application or use, are for all practical purposes indistinguishable from their natural counterparts. It is important to note that such synthetic and natural specimens are members of the same species, and are accordingly identical in their gross physical, chemical and structural properties. The term "synthetic" in the context of this invention therefore does not apply to specimens that are simulants, look-alikes, facsimiles or imitations.

Differentiation between gems of different species or between a gem specimen and a look-alike is readily done. For example, it is relatively easy to distinguish between an authentic ruby gemstone and a similarly cut and colored representative of the so-called garnet or spinel family. There are clear physical and chemical differences that produce macroscopic property differences that can be measured by common laboratory techniques and instruments such as refractometers (measurement of the refractive index), spectrometers, or density determinations and hardness measurements.

Strict identification (distinguishing between species) of gemstones is accomplished relatively easy since members of a species have rather identical nonvarying chemical composition and crystal structures. Since chemical composition and structure determine the physical properties, measurements of such gross physical properties yield the means for identification.

However, differentiation of gemstones of the same species, which differ from each other in origin (i.e., natural from synthetic) but not is gross physical, chemical or structural characteristics, poses a significant problem of a higher order. The finite differences that do exist are submicroscopic in character and occur at a level where atomic and electronic processes find their origin. Only in rare cases will such minor differences readily express themselves externally.

The more closely a growth environment of synthetic gemstones is related to that from which the natural specimens originated, and the closer the process is controlled chemically, physically and thermodynamically, the more readily synthetic specimens will be produced which are virtually impossible to differentiate from the best of their natural counterparts. For example, the best synthetic rubies are for all practical purposes indistinguishable from the best of natural rubies such as those from the Magok area of Burma or other fine specimens from Ceylon or Thailand.

A quality gemstone should be sufficiently beautiful to serve the purpose of personal adornment, and also should be durable to make its display lasting and enduring. This functionality of a gem is of course equally well served by a natural specimen as it is by a synthetic representative of equal beauty. However, there are other characteristics that set the natural specimen apart from the synthetic in the area of rarety, preciousness, authenticity, specific origin, value as an investment commodity and specific cost. In particular, the last two categories make it imperative that instrumented means exist to distinguish between naturals and synthetics. The best of natural stones may fetch prizes up to a thousand times that paid for synthetic specimens.

Synthetic stones have found their way into the channels of trade of natural stones. Exact duplicates of natural stones have been cut from synthetic raw material and have taken the place of previously certified natural materials. Similar exchanges occur with gems in mountings and settings.

At least four different growth processes—flame fusion, fluxed melt growth, hydrothermal techniques and solution growth—are capable of producing gem quality ruby and sapphire stones, and several processes are also known to yield high-quality emeralds. The number of manufacturers using these processes is increasing. Further, the value of colored stones as a trading and investment commodity is growing by leaps and bounds.

With thousands of gems of this type being traded each year, there is a clear need for instrumentation to quickly and efficiently differentiate between the products made by nature and by man.

Standard techniques and devices presently exist for distinguishing between natural and synthetic gemstones. Some of these techniques may be found in textbooks on the transmission of electromagnetic energy, as well as scanning electromicroscopy and light microscopy. These techniques make use of the known fact that synthetic gemstones approach perfection in atomic structure to a far greater extent than their natural counterparts. Several forms of radiation have also been used to directly or indirectly determine structural perfection of materials, including gamma rays, X-rays ultraviolet radiation, electron beams and radiation in the visible part of the electromagnetic energy spectrum. However, all of these approaches involve highly specialized and expensive equipment that require highly specialized training, pose availability problems, are limited by range of applicability and often require destructive specimen preparation. In addition, there are often size, orientation and surface quality requirements of the specimen which cannot be readily met by the product available in the trade.

There is to date no available apparatus which will, in one measurement, differentiate between natural and synthetic gemstones of the same species without regard to their size, shape, clarity, brilliance, morphology, color, cut or degree of finish, and which will do so without recourse to reference books, additional or supplemental measurements, and reliance on individual expertise and experience.

SUMMARY OF THE INVENTION

The analyzing apparatus according to the invention is based on the discovery that the total intensity of radiation from a gem specimen, as detected in a predetermined narrow spectrum, resulting from interaction of the gem specimen with a source of electromagnetic energy over a very broad spectrum, will differ significantly between natural and synthetic specimens of the same species. "Interaction" in this regard contemplates the combined processes of transmission and absorption of electromagnetic energy through and by the gem specimen, the reflection (diffraction) of energy internally of the specimen (which is to be distinguished from reflectance from a planar gem surface), and the emission of electromagnetic energy from the gem which results from internal excitation (e.g., fluorescence).

The intensity differences are primarily the result of differences in structure and bonding at the atomic level, which relate to structural perfection and quality. The degree of transmission, absorption, internal reflection and emission of radiation can, as compared to that in a hypothetical perfect crystalline specimen, be significantly reduced by a variety of characteristics directly related to the growth process, whether natural or synthetic. All such characteristics constitute a departure from order or perfection in the crystal and will directly or indirectly form barriers to the various electronic processes involved in transmission, absorption, internal reflection or emission of radiation.

Synthetic gems have a much higher degree of structural perfection or atomic order, and I have found that the intensity of radiation resulting from the full interaction of a broad spectrum of electromagnetic energy with gem specimens will be several order of magnitude greater for synthetic gems than for their natural counterparts. It is this discovery that permits simple and accurate analysis by discrimination and quantification.

Analog signals representative of intensity of output radiation from the gem specimen can be electronically processed to determine the origin of the specimen as well as to provide a quantitative output by which the specimen may be compared with others even in the same origin group.

In the inventive gem analyzing apparatus, a source of electromagnetic radiation interacts with a specimen, and the integrated response of such interaction energizes an appropriate detector, the output signal of which is processed through electronic circuitry, characterizing the stone as falling into broad quantified categories and thus determining origin. Operation of the instrument is not based on the measurement of any one physical property such as the value of the thermal conductivity, the reflective index, its dispersion, hardness, electrical conductivity, or the like, but rather on the specific generation, interpretation, processing and display of an integrated signal resulting from the interaction of the source of radiated energy and the sample.

The signal type (frequency and frequency distribution) and signal strength will be determined by several factors in two categories; viz., the intrinsic atomic structural character and characteristics of the apparatus itself.

The nature of the response due to its intrinsic character will depend on many physical properties of the specimen such as reflective index, dispersion, optical character, absorption coefficient and such features as clarity, inclusions, crystallinity and surface structure of the gem.

The parameters of the apparatus include the nature of the source of radiation, its intensity, the size of the aperture through which radiation is exposed to the gem specimen, detector characteristics and the like, all of which can in any one evaluation be kept fixed so as to provide a common base line. Since the total energy of interaction will be different from specimen to specimen, and since analysis is not dependent on the accurate determination of any one physical property, operation of the instrument is greatly simplified. Few, if any, restrictions are put on the nature of the specimen itself which otherwise would be required if measurement of a singular physical property were needed. As such, the apparatus does not specifically require a monochromatic source, special filtering, accurate focusing or manipulation of the beam, placement of a sample in a prescribed geometric arrangement, position or orientation, or the determination of nature and strength of the source of radiation. For these reasons, the inventive apparatus will accurately perform its analyzing function for specimens that are large or small, odd or regularly shaped or have various degrees of clarity or ranges of color, and operation is accomplished without the need for specific orientation, or cut or degree of finish of the specimen.

The analog signal may also be processed through an analog to digital converter to display a unitless, arbitrary number. Thus the inventive apparatus not only is capable of distinguishing between natural and synthetic gems, but also is capable of accurately and quantitatively relating specimens in a single origin group, enabling further differentiation in terms of other evaluation parameters such as brilliance, beauty, fire, quality or specific value. These unique features permit unlimited applications in other areas such as quality control, product reproduction, gem certification and "finger printing" of a particular gem.

The preferred embodiment is specifically directed to the selective discrimination and quantification of ruby and emerald gemstones, and is capable of two selective modes of operation.

Because of similarities in molecular structure, a single source of radiation may be used for both gems, while different reference values as determined by the electronic circuitry are selectively used based on the desired mode of operation. In the preferred embodiment, the source of radiation is a quartz envelope mercury discharge lamp which emits radiation in a broad spectrum of electromagnetic energy, the wavelength of which ranges at the low end from approximately 1800 Angstroms in the far-ultraviolet region through the visible region and into the near-infrared region. This particular lamp peaks at several individual wavelengths, the principal of which is 2550 Angstroms. Both natural and synthetic rubies undergo internal excitation (fluorescence), which produces a frequency shift and results in the emission of electromagnetic energy at approximately 6500 Angstroms. The detector used in connection with this particular lamp is a photocell (photoconductive or photoresistant cell) that senses electromagnetic energy in the narrow region around 6500 Angstroms.

The inventive apparatus does not require the use of any filters to isolate specific frequencies from the discharge spectrum of the radiation source. The presence of well-defined spectral intensities at frequencies across the emission spectrum enhances the process of discrimination according to the invention since differences in attenuation and specific frequencies add cumulatively to the level of the integrated signal. Stated otherwise, the photocell detector measures the cumulative effect produced by transmission, internal reflectance and internal excitation in the narrow range of 6500 Angstroms, the result of which is an analog signal which is directly proportional to the intensity of electromagnetic energy to which the photocell is exposed.

It is to be emphasized that the desired gem analysis could for any one species be accomplished by different sets of source-detector combinations. The electromagnetic energy source may, for example, generate accelerated electrons or other particles, X-rays, ultraviolet radiation, visible and infrared (heat) rays and radiation spanning the electromagnetic spectrum from the energy of gamma rays to that of the microwave region. The specific choice of a radiation source-detector pair will of course depend on the nature and extent of the differences in the basic characteristics intrinsic to each specimen for which discrimination is desired. A judicious choice will be influenced by other considerations such as cost, geometry, safety and other operational parameters. Since the principle on which the invention is based does not require that a specimen be specifically prepared, oriented, finished or have other geometric characteristics, there is no preference for any one source having a particular wavelength characteristic.

Preferably, optical filters are used between the gem and detector to mask the radiation from the gem except in the narrow detector wavelength range.

Also in the preferred embodiment, the gem specimen is supported on a holder that is fully opaque to the entire spectrum of source emission with the exception of an aperture which is sized to effectively limit energy throughout to an area equal to or smaller than the specimen in a direction perpendicular to the plane of the aperture. This is an important relationship to insure that whatever energy is detected by the photocell is emitted from the gem.

As suggested above, the detector is chosen so that its detectability and sensitivity are highest in the frequency range of radiation resulting from the source-specimen interaction as modified by the filters. In the preferred embodiment, this is a photoconductive (photoresistant) device or photocell that generates an analog signal directly proportional to the intensity of detected energy. Other detectors, such as phototransistors (photodiodes), scintillation counters, Faraday cups and photomultipliers may be used with other radiation sources or other gem specimens.

Because the radiation from a mercury discharge lamp is potentially dangerous to human eyes and skin, it is necessary for the inventive apparatus to be optically sealed during all phases of operation to preclude radiation leakage. In the preferred embodiment, this is uniquely accomplished by disposing a slidable specimen drawer between the mercury discharge lamp and the photocell detector, and providing a mechanical shutter mechanism between the drawer and lamp and between the drawer and photocell. The shutter mechanism is actuated only when the drawer is fully closed and latched, at which time registration of the several apertures included in the shutter mechanism are disposed in registration.

This provision for optical sealing also permits the mercury discharge lamp to operate continuously during the analysis of a number of specimens. This is advantageous since the mercury discharge lamps, and other appropriate discharge sources, require a significant period of warmup before stabilized operation occurs, and turning it off after each analysis would slow the analysis of a number of specimens considerably. In addition, repeated on-off operation reduces the life of the discharge lamp.

A gem analyzing apparatus made in accordance with the invention is easily operated by persons without specific knowledge, experience or expertise. The user may quickly and accurately utilize the apparatus to distinguish natural specimens from synthetic specimens for a particular species, to quantify a plurality of gem specimens with any particular origin group, to "fingerprint" a gem of a particular species, and to detect whether a particular specimen is or is not within a particular species. It is also possible to substitute other radiation sources for the mercury discharge lamp of the preferred embodiment to provide all of the foregoing functions for gems other than rubies and emeralds.

BRIEF DESCRIPTION OF THE DRAWINGS

FIG. 1 is a view in side elevation of the inventive gem discriminating apparatus;

FIG. 2 is a view in top plan of the gem discriminating apparatus;

FIG. 3 is a view in rear elevation of the inventive apparatus;

FIG. 4 is a view in front elevation of the inventive apparatus;

FIG. 7 is a sectional view taken along the line 7—7 of FIG. 5;

FIG. 8 is a sectional view taken along the line 8—8 of FIG. 5;

FIG. 9 is an enlarged fragmentary sectional view similar to portions of FIG. 5;

FIG. 10 is an enlarged fragmentary perspective view of a holder for the gem specimen to be analyzed and the support from which it may be moved;

DETAILED DESCRIPTION OF THE INVENTION

Figure 5:
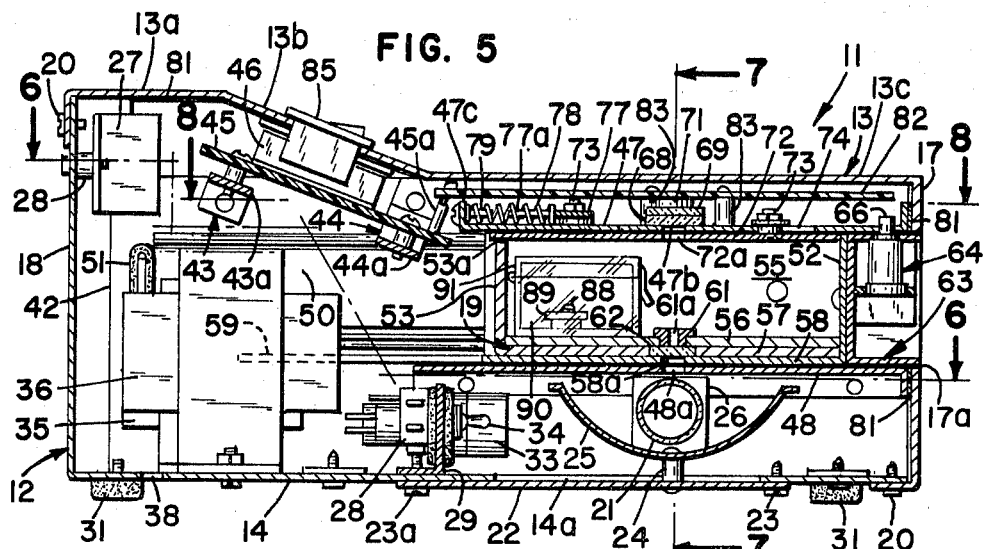
FIG. 5 is a sectional view of the apparatus taken along the line 5—5 of FIG. 2.

With initial reference to FIGS. 1–4, a digital gem analyzer is represented generally by the numeral 11. In the preferred embodiment, the gem analyzer 11 comprises a cabinet 12 formed from metal stamping and having a top 13, bottom 14, left and right sides 15, 16, respectively, a front 17 and back 18. A single plate member defines the top 13, and front 17, the top defining an upper horizontal section 13a, an intermediate, inclined display section 13b and a lower horizontal section 13c.

The front 17 is formed with a rectangular opening 17a (FIG. 4) to accommodate a drawer 19 (shown in phantom in FIGS. 1 and 2), in which a gem specimen is placed for analyzing. As will become apparent below, the inside of the cabinet 12 is optically sealed with the drawer 19 in both open and closed positions, with analysis taking place with the drawer closed.

As shown in FIG. 5, a single plate member forms the sides 15, 16, the bottom 14 and back 18, and this member receives and supports tabs at each end of the plate member defining the top 13 and front 17 through the use of screws 20.

Figure 6:
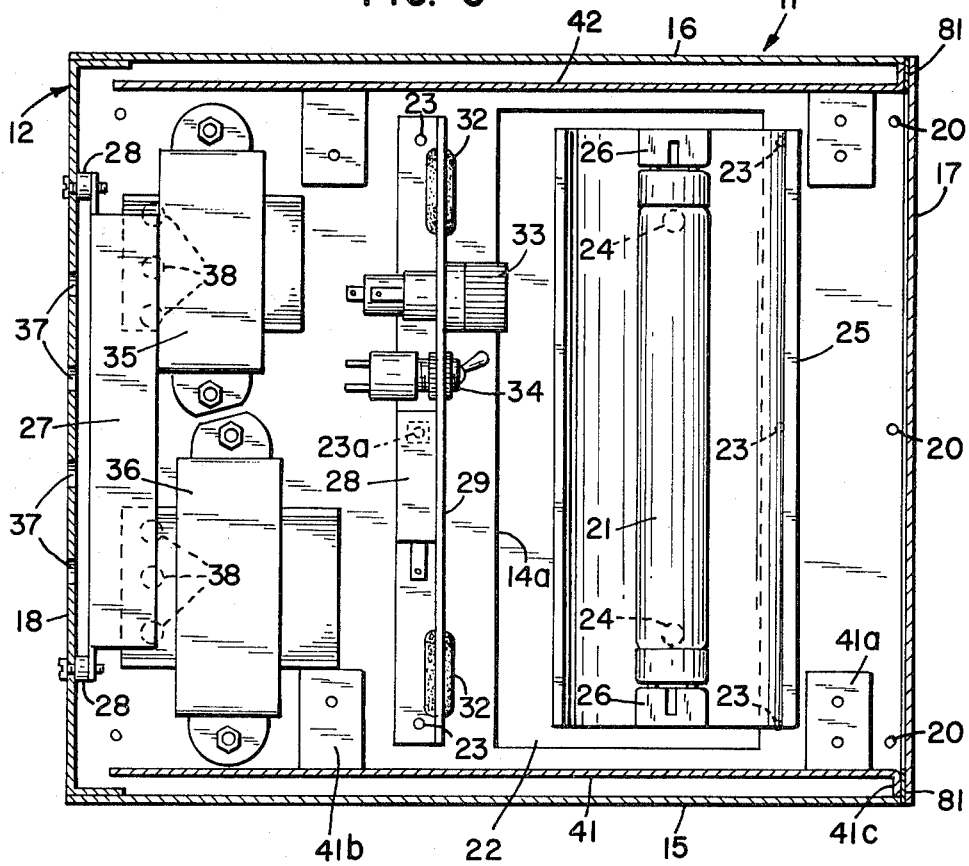
FIG. 6 is a sectional view taken along the line 6—6 of FIG. 5.

With reference to FIGS. 5 and 6, a large rectangular opening 14a is formed in the bottom 14 toward the front of cabinet 12 to serve as an access opening to a source of electromagnetic radiation. In the preferred embodiment, the source is an unfiltered quartz mercury discharge tube lamp 21 that generates radiation over a broad spectrum of electromagnetic energy, the wavelength of which ranges from approximately 1800 Angstroms in the far-ultraviolet region at the low end through the visible region and into the near-infrared region. Discharge tube lamp 21 is replaceably mounted in a manner described in detail below.

Rectangular opening 14a is normally closed by a slightly larger cover plate 22 that is secured to the bottom 14 by screws 23. A pair of mounting studs 24 are secured to the cover plate 22, projecting internally to carry a parabolic reflector 25 for the lamp 21. Lamp holders 26 are suitably mounted to each end of the reflector 25 to support the lamp 21 thereabove in a position in which radiated energy will be openly reflected in an upward direction.

Voltage is applied to the lamp 21 through a ballast transformer 27 that is mounted in spaced relation along the inner top surface of back 18 by brackets 28 (FIGS. 5 and 6). The electrical circuitry connecting the power supply, lamp 21 and ballast transformer 27 is shown in detail in FIGS. 12 and 13. The conductors have been deleted from the structural figures for purposes of clarity. However, the electrical circuitry also includes a microswitch 28 (FIGS. 5 and 6) that is secured to an elongated, L-shaped bracket 29 mounted to the top surface of bottom 14 and extending over a substantial portion of its width. The microswitch 28 is disposed in overlying, engageable relation to one of the mounting screws 23 (reference numeral 23a) for the cover plate 22. The microswitch 28 is normally biased to an electrically open position, and urged closed by the screw 23a, so that withdrawal of the mounting screw 23a for purposes of removing the cover plate 22 causes an open condition in the power supply to lamp 21.

As constructed, removal of the cover plate 22 interrupts power to the lamp 21, the radiation from which is potentially dangerous to human eyesight and skin. Because the reflector 25 and lamp holders 26 are mounted to the cover plate 22, its removal also permits easy replacement of the source lamp 21 in case of failure or when a different type of source emission is required.

Rubber feet 31 (FIGS. 1, 3 and 5) are secured to the undersurface of bottom 14 at each corner.

As best shown in FIG. 6, the elongated mounting bracket 29 is also used to support a pair of grommets 32 for guidably retaining internal electrical conductors, a circuit fuse 33 and a switch 34 that diverts the applied circuit voltage between 110 volts and 220 volts, depending on the available source. The fuse 33 and switch 34 are discussed below in connection with the electrical circuit diagram of FIG. 12.

With continued reference to FIGS. 5 and 6, a pair of transformers 35, 36 are mounted internally of the cabinet 12 on the bottom 14 generally below the ballast 27. The transformer 35 serves to reduce a standard supply of 110 volts to a 12 volt supply to the control circuitry. The transformer 36 is used in conjunction with the switch 34 to provide a supply of 110 volts to the apparatus where the input voltage is 220 volts. The transformers 35, 36 are operationally described in conjunction with FIG. 12.

A plurality of vent holes 37 are formed in the back 18 rearwardly of the ballast transformer 27, as shown in FIG. 3. Two sets of vent holes 38 are formed in the bottom 14 behind the transformers 35, 36, as shown in FIGS. 5 and 6. The vent holes 37, 38 are positioned so that they are masked by internal components to prevent the leakage of radiation, while at the same time permitting ventilation of heat generating internal components.

With reference to FIG. 6, a pair of internal side support walls 41, 42 are mounted in spaced relation to the respective side walls 15, 16. These support walls are mirror images and a description of the wall 41 will be exemplary of both. Wall 41 includes a pair of angled tab feet 41a, 41b that are secured to the upper surface of bottom 14 to hold the wall in its rigid upstanding position. The front edge of the wall 41 is bent outwardly to define a spacer flange 41c.

The support walls 41, 42 together serve as the foundation for a number of internal frame members and supports. These include a pair of elongated brackets 43, 44 that extend crosswise of the walls 41, 42 and are disposed below the inclined sections 13b of top 13. Each of the brackets 43, 44 includes a flat section (FIG. 5) that extends over a substantial portion of the distance between the support walls, and which is disposed in parallel relation to the inclined section 13b. These two sections, which bear the reference numerals 43a, 44a, are coplanar and together offer support to a printed circuitboard 45 that carries a portion of the electronic control circuitry, including a liquid crystal display 46. The display 46 is viewed through a rectangular opening 13d formed in the inclined section 13b.

With reference to FIG. 7, also secured to and extending between the support walls 41, 42 are a pair of horizontal support plates 47, 48 that are mounted immediately above and below the drawer 19, respectively. As best seen in FIG. 7, a pair of ball bearing drawer guides 49, 50 are secured to the support walls 41, 42 between the support plates 47, 48, extending rearwardly along each side. The drawer 19 is secured to the movable portion of each guide 49, 50, permitting it to move freely between open and closed positions. As shown in FIG. 5, a rubberized drawer stop 51 is disposed at the extreme inner end of the guide 50 to cushion the drawer 19 as it reaches the closed position. Guide 49 includes a similar stop which is not shown.

With reference to FIGS. 5, 7 and 9, drawer 19 is also formed from thin metal plate, and comprises a front 52, back 53, lefthand side 54 (FIG. 7 only) and righthand side 55. The bottom is compound, including upper, middle and lower bottom plates 56–58, respectively. For constructional purposes, the middle bottom plate 57 is integrally formed with the drawer back 53, and the lower plate 58 is integrally formed with the drawer front 52. All three of the bottom plates 56–58 are rectangular in shape, but plate 58 also includes a rearwardly projecting tongue 59 (see also FIG. 8).

Centrally disposed, coaxial apertures of different size are formed in each of the plates 56–58. The uppermost aperture, which bears the reference numeral 56a, is of intermediate size and loosely receives a specimen holder 61 having an axially extending aperture 61a formed therethrough (see also FIG. 10). The middle plate 57 has an aperture 57a into which a disc 62 is placed. The disc 62 is made from material that is fully transparent to the entire frequency range of the radiation source 21 to insure that the gem specimen is fully exposed to the entire range. For mercury discharge ultraviolet sources, the disc 62 is made from high transparency quartz. The function of disc 62 is to prevent the accidental dropping of a gem specimen or other article into the internal portions of the cabinet 12 when the specimen holder 61 is removed, as well as to reduce the entry of dust and other particulate matter into the cabinet 12.

The lower plate 58 is formed with the smallest aperture 58a.

With continued reference to FIG. 9, the lower plate 48 is also formed with an aperture 48a that is disposed immediately above the ultraviolet lamp 21. Further, and as additionally shown in FIG. 5, the drawer is constructed and disposed so that the apertures 58a, disc 62, specimen holder 61 and aperture 61a directly overlie the aperture 48a when the drawer 19 is in the closed and latched position. As such, radiation from the lamp 21 is exposed directly to a gem resting on the specimen holder 61. However, for all other positions of the drawer 19, either the tongue 59 or the main portion of the plate 58 directly overlies the lamp 21, precluding exposure of radiation to the gem specimen.

With reference to FIGS. 4 and 9, drawer 19 includes a drawer front 63 which takes the general form of a rectangular, forwardly facing open box and houses a latch assembly 64. This latch assembly comprises a vertically movable handle 65 to which a vertically projecting latch element 66 (FIG. 9 only) is connected. As best shown in FIG. 4, the handle 65 comprises a symmetrically formed metal strip generally taking the form of a W, and includes two valleys or recesses permitting the user to depress the handle 65 with two fingers.

The latch element 66 is slidably retained within a bushing or guide 67, which also houses a coil spring (not shown) that normally urges the latch element 66 and handle 65 into the position shown in FIG. 9. Downward movement of the handle 65, as shown in FIG. 4, causes the latch element to withdraw into the guide 67 in a position that is flush with the top surface of the drawer front 63.

As shown in FIG. 9, the upper support plate 47 has an aperture 47a centrally disposed along its front edge for registration with the latch element 66. Both the latch element 66 and aperture 47a are circular in configuration, and the outer cylindrical surface of latch element 66 is vertically disposed. Consequently, the drawer 19 can only be completely closed by depressing the handle 65 and pushing it to the fully closed position. Release of the handle 65 at this time will enable the latch element 66 to project into the aperture 47a to lock the drawer 19 in the closed position. This position is shown in FIG. 5.

With continued reference to FIG. 9, the upper support plate 47 has a second circular aperture 47b which is centrally disposed in coaxial relationship with the aperture 48a. Mounted immediately above the aperture 47b are two optical filters 68, 69 and a photocell 71, all of which are disposed in a position to receive radiated energy from the lamp 21 with the drawer 19 in closed position.

With reference to FIGS. 8 and 9, a rectangular metal plate 72 is slidably mounted on the undersurface of upper support plate 47, extending longitudinally rearward from a point just behind the aperture 47a. Plate 72 is capable of limited longitudinal sliding movement by reason of its mounting, which includes three nut and bolt assemblies 73 projecting through three elongated slots 74–76 formed in the upper support plate 47. A small transverse strap 77 extends between the assemblies 73 associated with slots 75, 76 and includes a rearwardly projecting finger 77a. A coil spring 78 is mounted in compression between the finger 77a and a forwardly projecting screw 79 that is mounted in an upstanding flange 47c formed on the rear edge of the upper support plate 47. As constructed, the coil spring 78 urges the strap 77 and rectangular plate 72 forward into the position shown in FIG. 9 when the drawer 19 is open.

Rectangular plate 72 also includes a circular aperture 72a capable of registering with the aperture 47b when the drawer 19 is closed (FIG. 5). This rearward sliding movement of the plate 72 against the bias of spring 78 occurs when the drawer front 52 strikes the front edge of the plate 72 when the drawer 19 is being closed. A shallow rectangular recess or slot 53a (FIG. 9) is formed in the upper central edge of the drawer back 53 to prevent engagement by the back 53 with the plate 72 as the drawer 19 is being closed.

The aperture 72a is positioned within the plate 72 so that registration with the aperture 47b is accomplished when the drawer 19 reaches its fully closed position. As discussed above, registration is simultaneously accomplished with the lower group of apertures 48a, 58a, the quartz disc 62 and aperture 61a. This aperture registration system which acts as a mechaical shutter, is designed to optically seal the cabinet 12 during all phases of operation of the apparatus, and regardless of the position of the drawer 19. This not only constitutes a safety feature, eliminating the possibility of leakage of potentially harmful radiation, but also permits the mercury discharge lamp 21 to operate continuously. Lamps of this type generally do not reach a level of stable operation for several minutes, and it is highly inefficient if the lamp must be turned off after analysis of each gem specimen.

Optical sealing of the cabinet is also enhanced by the use of sealing tape strips 81 that are disposed between the front 17 and each of the front edges of the support plates 47, 48 (FIG. 9) between the front 17 and each of the sides 15, 16 (FIGS. 1 and 6) and between the top 13 and the upper edge of each of the sides 15, 16 (FIG. 1).

With reference to FIGS. 8 and 9, a second printed circuit board 82 is mounted in spaced relation between the top 13 and upper support plate 47 by three spacers 83 that surround the aperture 47b, filters 68, 69 and photocell 71. The photocell 71 is mounted on the bottom side of printed circuit board 82, and the filters 68, 69 are frictionally held against the upper surface of support plate 47.

A multiple connector strip 45a establishes the appropriate electrical connections between the rear edge of printed circuit board 82 and the leading edge of printed circuit board 45.

The inclined or readout section 13b of the top 13 also serves as a mount for a pair of rocker switches 84, 85, the former of which serves to turn the apparatus on and off, and the latter of which permits mode selection as described in further detail below. Also mounted within the display section 13b are a calibration potentiometer 86 and a light emitting diode 87 indicating "source on".

The calibration potentiometer 86 is used in conjunction with a calibration gem specimen 88 (FIG. 5), which is permanently secured to a calibration specimen holder 89 disposed in a closed box 90 having a hinged top 91. The box 90 is removably disposed in one corner of the drawer 19. The calibration operation is described more fully below.

Figure 11:
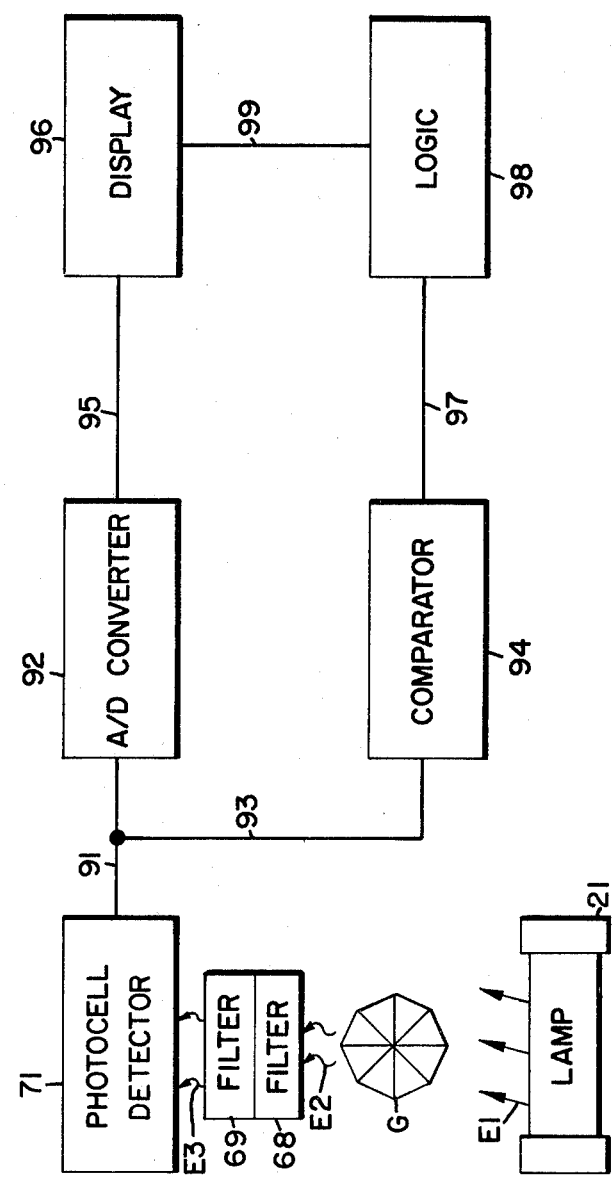
FIG. 11 is a block diagram of the electrical and electronic signal processing aspects of the apparatus.

FIGS. 11–16 disclose the electronic circuitry for analyzer 11. FIG. 11 is a block diagram disclosing the mercury discharge lamp 21, a gem specimen G, red and blue glass optical filters 68, 69, respectively and the photocell detector 71. Lamp 21 radiates a broad spectrum of electromagnetic energy as shown at E1. E2 represents the electromagnetic radiation from the gem specimen G, which is a function of the total interaction of the gem specimen G with the energy E1. This takes into account the electromagnetic energy transmitted through and absorbed by the gem G, the internal reflection of energy within the gem G and the electromagnetic energy emitted from the gem G by flourescence and/or other internal excitation.

The electromagnetic energy E3 passes through the filters 68, 69, and electromagnetic energy E3 falls upon the photocell detector 71. Detector 71, which comprises a photocell and voltage divider, generates an analog voltage signal that is transmitted through a conductor 91 to an analog to digital converter 92. The same analog voltage signal is transmitted through a conductor 93 to a comparator 94.

The analog to digital converter 92 converts the analog voltage from detector 71 into a digital binary coded signal which is in turn transmitted through a conductor 95 to a liquid crystal display (LCD) 96. The electronic circuits of comparator 94 analyze the analog voltage input from detector 71 and generate one of several signals through a plurality of conductors represented generally by the numeral 97. These conductors 97 lead to logic circuitry 98, which analyzes the several signals from comparator 94 and generates appropriate display signals through a plurality of conductors represented generally by the numeral 99 leading to the display 96. Thus, display 96 causes the display of a unitless, arbitrary decimal number (preferably three seven-segment digits) in response to the input from the analog to digital converter 92, and also displays one or more of six annunciator symbols or indicators in response to the signals from logic circuitry 98, as will be discussed in further detail below.

Figure 12:
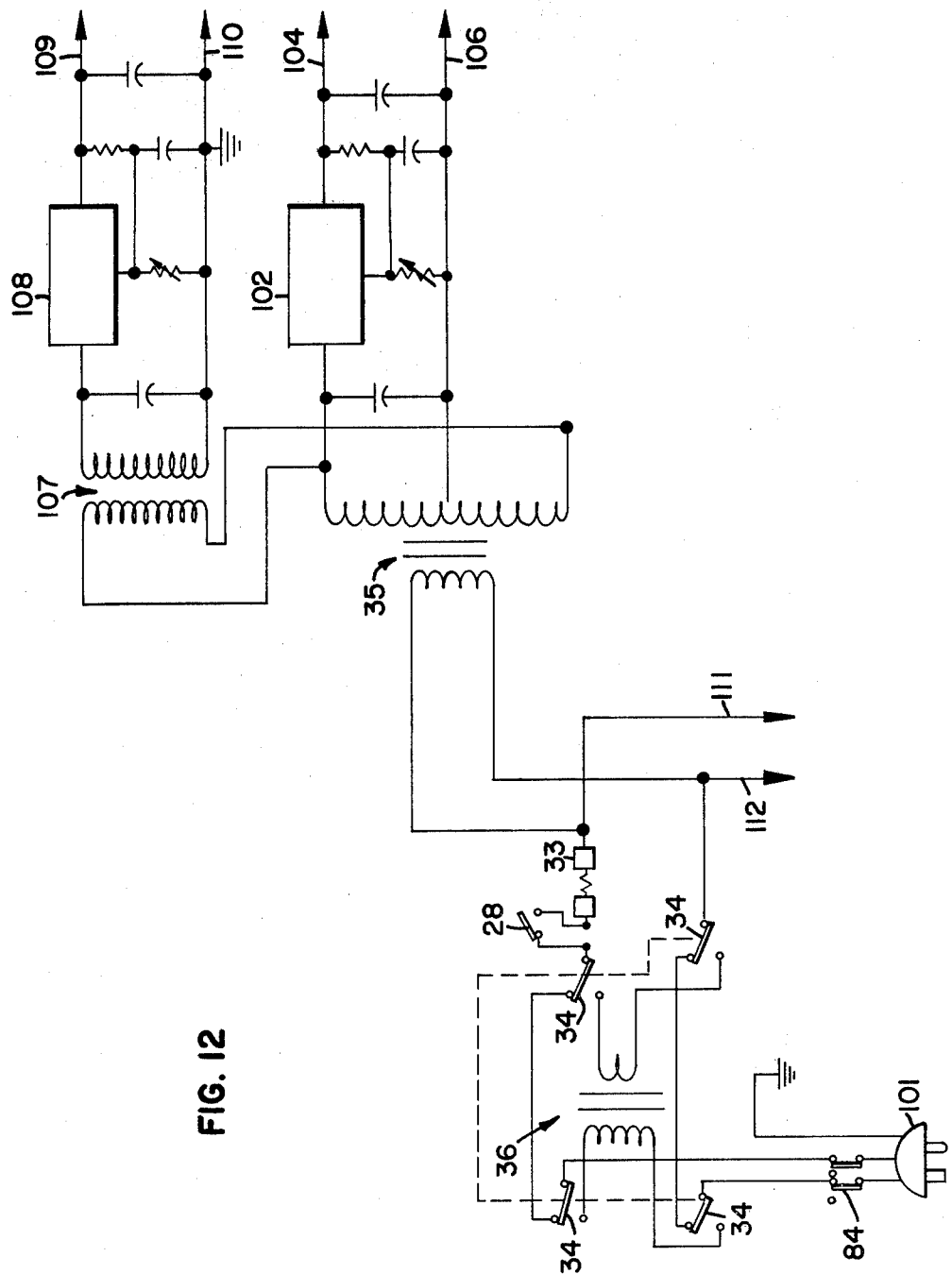
FIG. 12 is a schematic diagram of the power supply for the electrical and electronic circuitry of the apparatus.

FIG. 12 is a schematic representation of the power supply which provides regulated DC voltages to the various analog and digital circuits of the apparatus. Rocker switch 84 leads from a standard plug 101, which is connected either to a 120 volt, 60 Hz source, or to a 220 volt, 50 Hz source. Switch 34 selects the appropriate voltage, either providing the 110 volt, 60 Hz supply directly to the fuse 33 to transformer 35, or stepping down the 220 volt, 50 Hz supply to the 110 volt level through the transformer 36. The interlock microswitch 28 for cover plate 22 is connected between relay 34 and fuse 33 so that lamp 21 may be energized only when the cover plate 22 is properly in place, as discussed above.

Transformer 35 steps the 110 volt supply down to 28 volts rms, and this output is center tapped and delivered to a voltage regulator 102, to deliver +12 volts to the system analog circuits through a conductor 104. Conductor 106 serves as a ground.

The output of transformer 35 is also connected to the transformer 107, which in turn delivers 14 volts rms to a voltage regulator 108 to produce a +9 volts digital logic supply voltage on conductor 109. A conductor 110 serves as a ground conductor for this supply circuit. Voltage regulators 102 and 108 are both LM317 three-terminal adjustable regulators available from National Semiconductor Corporation, 2900 Semiconductor Drive, Santa Clara, Calif. 95051.

Figure 13:
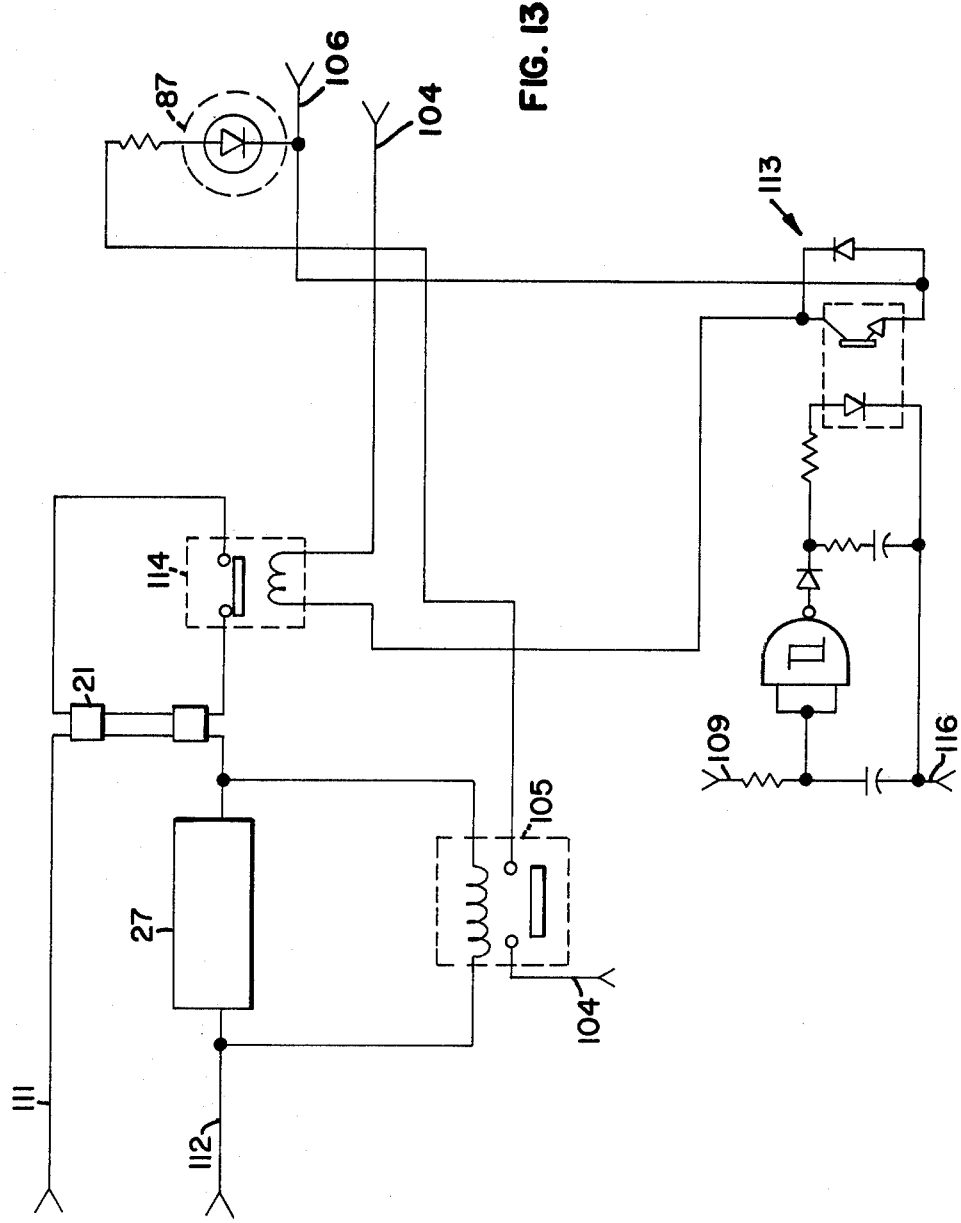
FIG. 13 is a schematic diagram of the electrical and electronic circuitry relating to the electromagnetic discharge source.

The circuitry associated with the mercury discharge lamp 21 is shown in FIG. 13. Conductors 111, 112 (see also FIG. 12) lead from the fused supply of 110 volts AC to the lamp 21 through the serially connected ballast transformer 27. Lamp start-up circuitry 113 provides a 5 second warmup stimulus to lamp 21 through a relay 114 when the apparatus is supplied with power. The "lamp on" indicator 87 is a light emitting diode (LED) which is driven through the relay 105 whenever the ballast voltage corresponding to an energized lamp condition is developed across ballast transformer 27. Conductor 116 originates in FIG. 14 and provides ground potential to circuitry 113.

Figure 14:
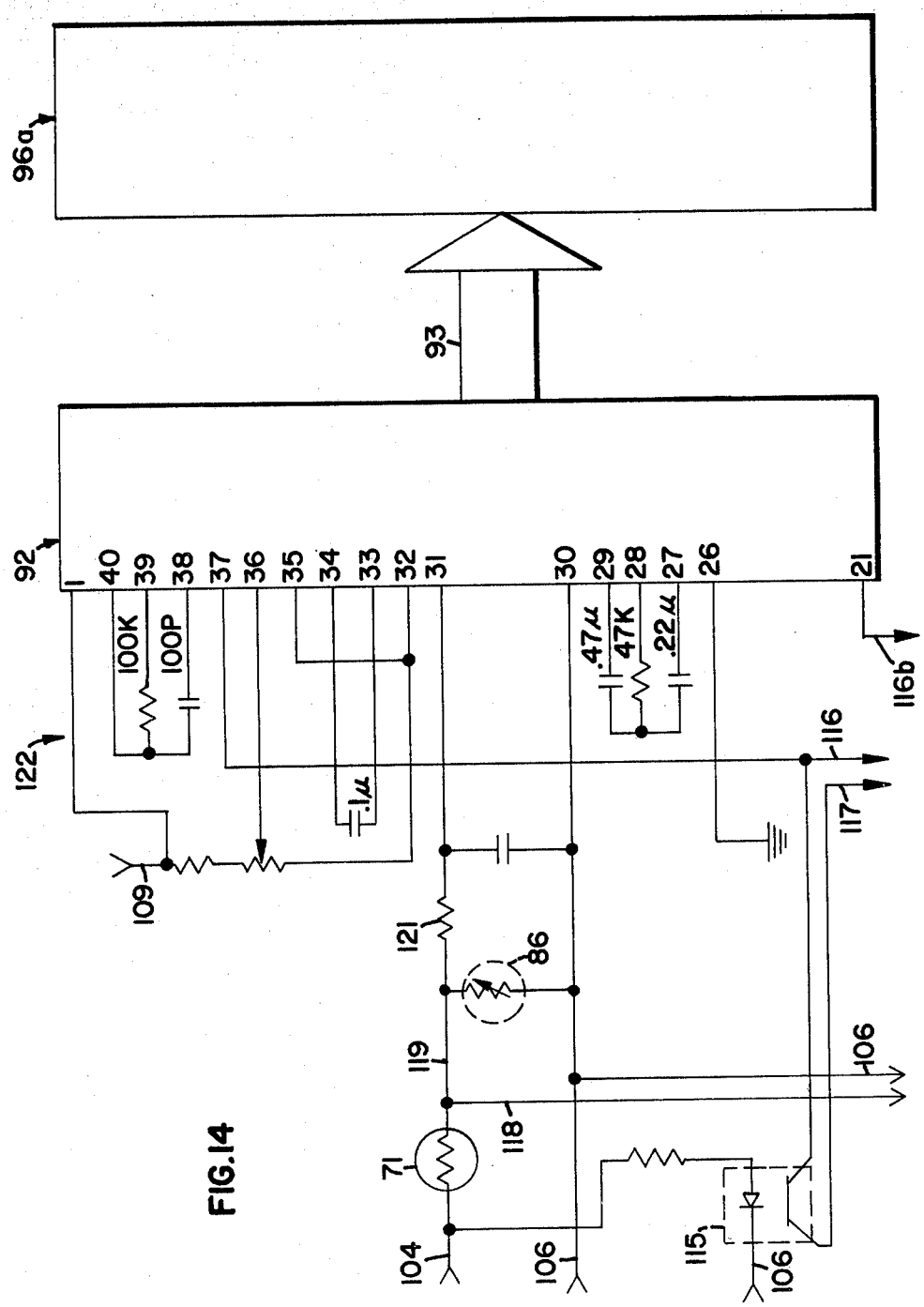
FIG. 14 is a schematic diagram of a portion of the electronic circuitry including the photocell detector, an analog output, an analog to digital converter and a display.
Figure 15:
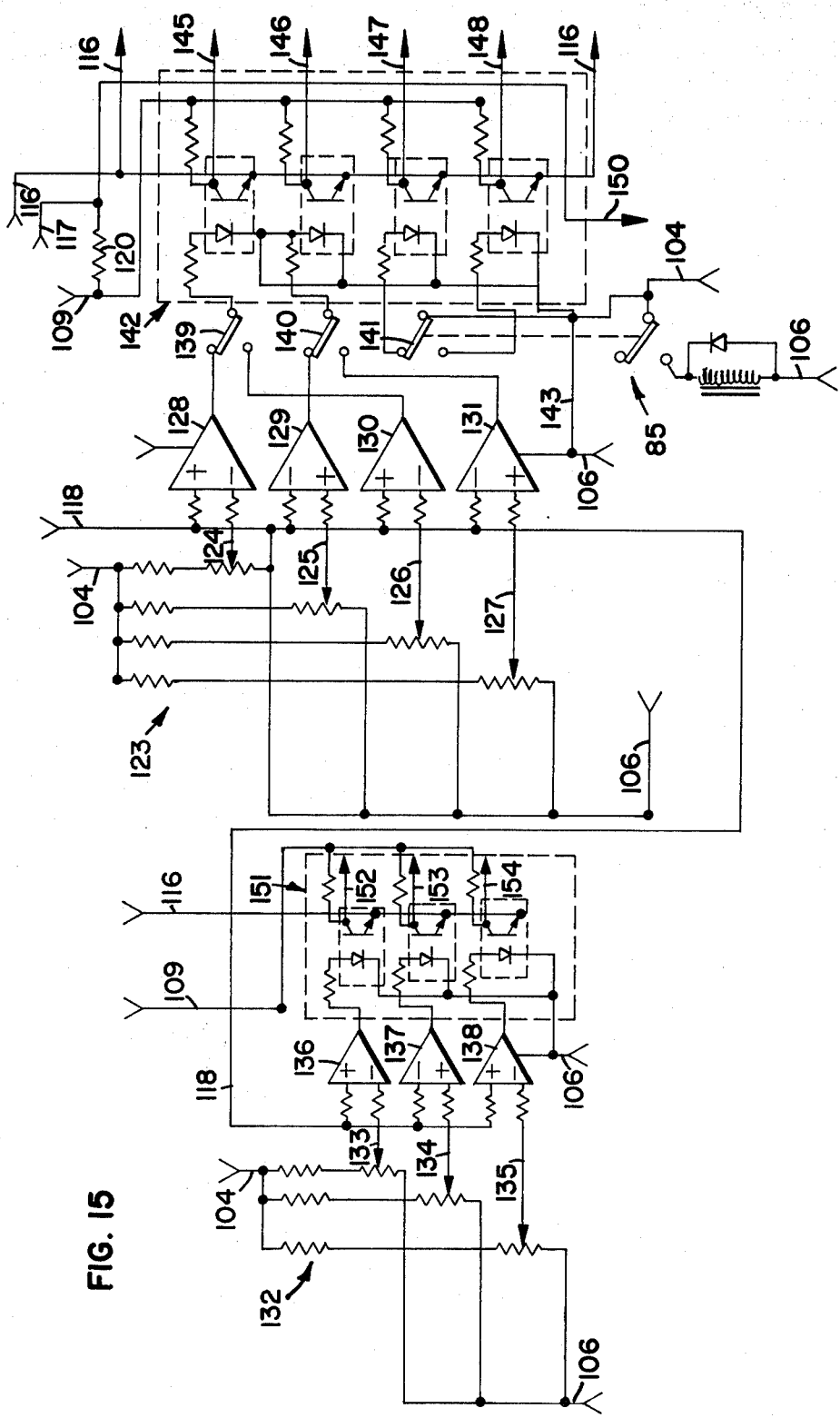
FIG. 15 is a schematic diagram of the electrical and electronic comparator circuitry that quantifies the analog output from the photocell and generates appropriate signals.

FIG. 14 discloses the circuitry associated with photocell detector 71 and the three digital decimal display portion of display 96, which bears the reference numeral 96a. Also shown in FIG. 14 but not directly related to this circuitry is an optical isolating transistor 115, which works in cooperation with the logic circuitry shown in FIG. 16 to indicate proper DC power supply operation. The emitter of isolating transistor 115 is tied to a ground conductor 116 with the collector connected to a conductor 117. As shown in FIG. 15, conductor 117 is connected to the +9 volt supply through a pullup resistor 120, and also to a conductor 150 described below.

One side of the photocell detector 71 is connected to the +12 volt conductor 104 from FIG. 12. The other side of detector 71 is connected to conductors 118 and 119. Conductor 119 is connected to the calibration potentiometer 86 (FIG. 2) and also to the input (pin 31) of the analog to digital converter 92 through a resistor 121 having a very high resistance value. Analog to digital converter 92 is a ICL7106 3½ Digit Single Chip A/D Converter manufactured by Intersil, Inc., Cupertino, Calif. The calibration potentiometer 86 provides adjustment or calibration of the photocell 71 output signal as discussed below. The other side of calibration potentiometer 86 is connected to the ground conductor 106.

The external components to the analog to digital converter 92 are represented generally by the numeral 122. These components provide reference voltages, readings/second control, auto zero capacitance and integration circuitry to the converter 92. The output of analog to digital converter 92 is encoded with a three digit decimal number and is formatted to drive the three seven-segment displays of the display 96 through conductors 93.

FIG. 15 discloses the circuitry associated with the upper and lower limit voltage comparator functions which determine gem classification in the analyzer 11. A voltage divider network 123 is powered by +12 volts (reference numeral 104) to provide reference voltages at conductors 124–127. The circuit includes four operational amplifiers 128-131. The conductors 124 and 126 are connected to the inverting input of operational amplifiers 128, 130, respectively, and the conductors 125 and 127 are connected to the noninverting inputs of operational amplifiers 129, 131, respectively. The conductor 118, which leads from the photocell detector 71 (FIG. 14) and carries the integrated analog signal, is connected to the noninverting inputs of operational amplifiers 128 and 130, and to the inverting inputs of operational amplifiers 129 and 131.

A voltage dividing network 132 provides three reference voltages at conductors 133-135. Three operational amplifiers 136-138 are connected to this network, the conductors 133 and 135 being connected to the inverting input of operational amplifiers 136 and 138, respectively, and the conductor 134 being connected to the noninverting input of operational amplifier 137. Conductor 118 extends beyond the operational amplifiers 128-131 as shown, and is connected to the noninverting input of operational amplifiers 136 and 138, and to the inverting input of operational amplifier 137.

The outputs of the operational amplifiers 128-131 are multiplexed through a pair of double pole-single throw relays, into the respective upper two inputs of a level shifting inverter network 142. A double pole, single throw relay 141, which is ganged with relays 139 and 140, selectively connects +12 volts through a conductor 143 to either one of the two lower inputs to level shifting inverter network 142.

Operational amplifiers 128, 129 represent a first pair and operational amplifiers 130, 131 represent a second pair, either pair of which may be selectively operated by the rocker switch 85 (see also FIG. 2), which is electromagnetically connected to the ganged relays 139 and 140. This permits operation of the apparatus 11 in "mode 1" or "mode 2". With the switch 85 open as shown in FIG. 15, the amplifiers 128, 129 are operational, and closing of the switch 85 causes the amplifiers 130, 131 to become operational.

Each of these pairs of amplifiers compares the analog voltage signal appearing on conductor 118 with the reference voltages on conductors 124, 125 to operate in a desired manner. In the preferred embodiment, if the voltage on conductor 118 is less than a predetermined low reference voltage, amplifier 128 turns "on", and the resulting signal is transmitted through the level shifting network 142 to the logic circuitry shown in FIG. 16. If the voltage level on conductor 118 is greater than a predetermined high reference voltage, amplifier 129 turns "on", and its output is transmitted through the level shifting network 142 to the logic network of FIG. 16. If the voltage level on conductor 118 falls between the low and high reference voltages, neither of the amplifiers 128, 129 turns "on" and this condition may be logically sensed by the logic circuitry of FIG. 16.

Selection of the amplifiers 130, 131 results in operation in "mode 2", which results in comparison of the voltage level on conductor 118 with the reference voltages appearing on conductors 126, 127. "Mode 2" operation is similar to that of "mode 1" in that amplifier 130 turns on if the signal voltage on conductor 118 is less than a predetermined low reference voltage on conductor 126, and amplifier 131 turns on if the signal voltage on conductor 118 is greater than a predetermined high reference voltage on conductor 127. Neither of the amplifiers 130, 131 turns on if the signal voltage on conductor 118 falls between the low and high reference voltages on conductors 126, 127.

Figure 16:
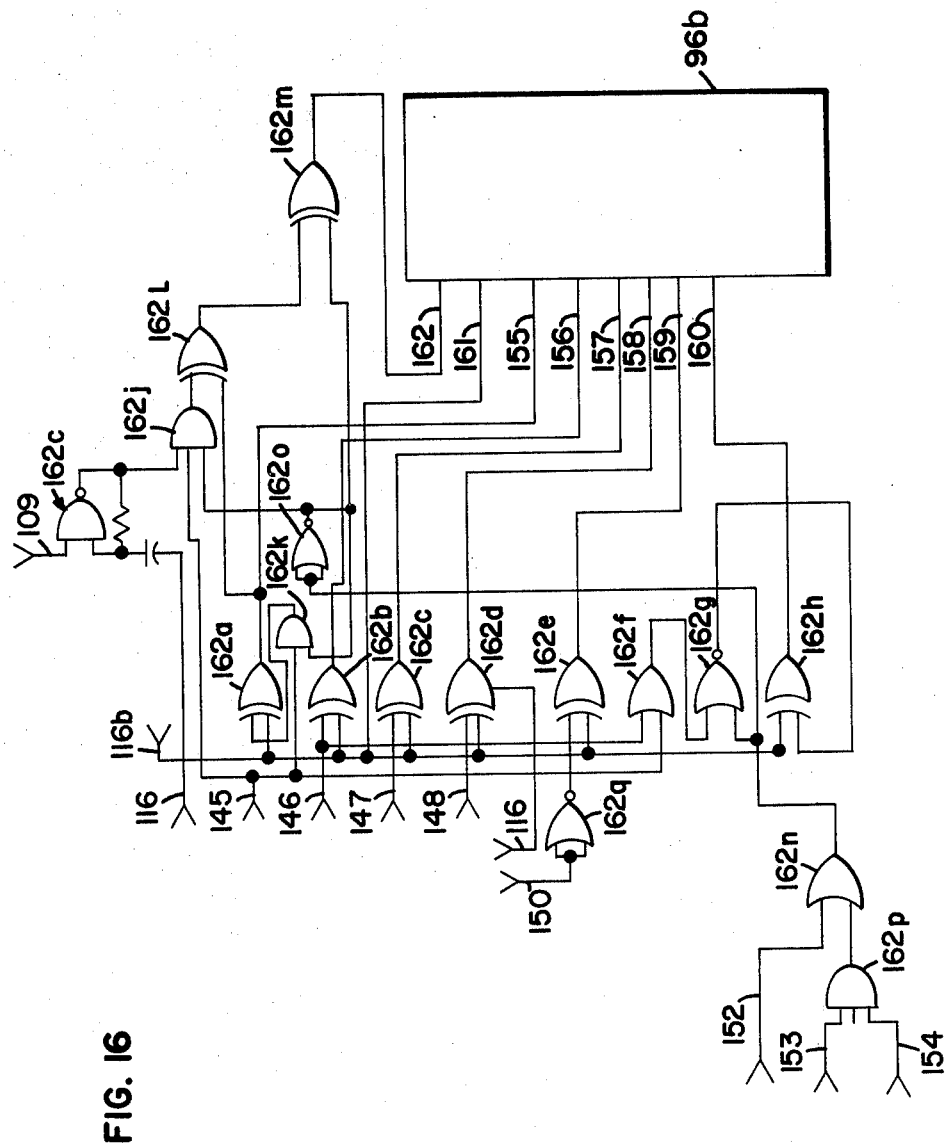
FIG. 16 is a schematic diagram of logic components that receive and process signals from the comparator circuitry and operate the display.

In either mode of operation, a plurality of output signals are transmitted through a plurality of conductors 145-148 to the logic circuitry of FIG. 16. The signals appearing on conductors 145-148 are derived from the voltage level on conductor 118 and operational condition of the amplifier pairs 128, 129 or 130, 131. Conductor 150 is connected directly to conductor 117, which is connected to the collector of transistor 115 (FIG. 14).

Operational amplifiers 136-138 act as a comparator in much the same way as the amplifiers 128-131, generating output signals through a level shifting inverter network 151 to output conductors 152-154. While the operational amplifiers 128-131 are intended to analyze the signal on conductor 118 to determine the nature and quality of the gem specimen G, the amplifiers 136-138 are specifically intended to generate an output indicative of a spurious or abnormal condition, as evidenced by the voltage level on conductor 118.

More specifically, the voltage level on conductor 118 will be at a spurious level if there is no gem specimen G on the gem holder 61, or abnormally low if the radiated energy is blocked for any reason before it reaches the photocell detector 71. For the latter case, amplifier 136 turns off if the voltage level on conductor 118 is less than a predetermined low reference voltage.

For the case where there is no gem specimen overlying the test aperture 61a, the reference voltages at conductors 134 and 135 are set to define a very narrow range corresponding to the spurious voltage level mentioned above. If the voltage level on conductor 118 falls within this narrow "window", both amplifiers 137 and 138 turn on to generate appropriate signals on the output conductors 153 and 154 as discussed in further detail below.

With reference to FIG. 16, the conductors 145-148 and 152-154 are input to a plurality of logic elements 162a-162q connected to generate desired outputs on conductors 155-162 (described in detail below), all of which lead to the display 96b. The displays 96a, 96b are integrated into a single display 96, the format of which is shown in FIG. 17.

Figure 17:
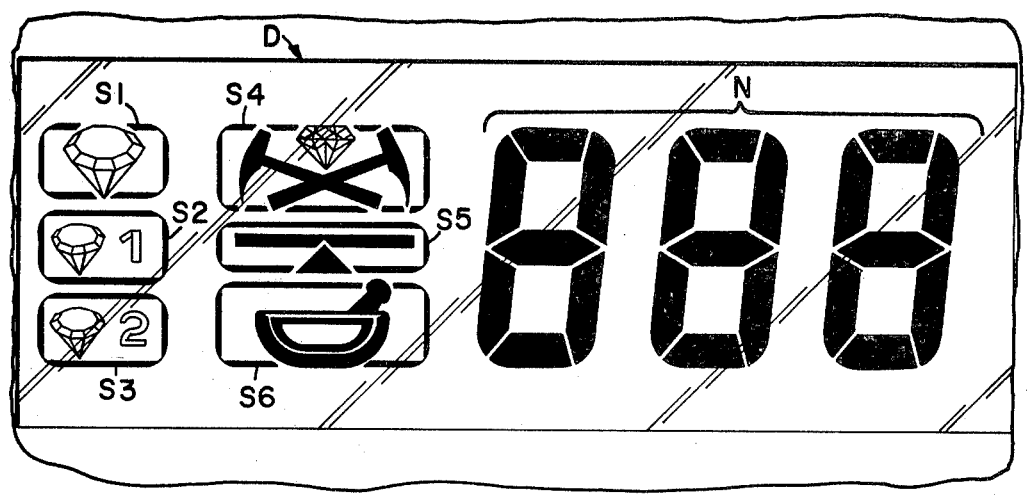
FIG. 17 is a graphic representation of the display or readout.

FIG. 17 discloses the entire display format of the liquid crystal display 96, which is represented generally by the reference letter D. In the display D, the unitless, arbitrary decimal number comprises three seven-segment digits and is represented by the reference numeral N. Display D also includes six annunciator symbols S1-S6 that are selectively displayed depending on the status and mode of operation of the apparatus and the nature of the gem specimen.

Symbol S1 comprises a gem in a rectangular frame and is displayed on the display D when the rocker switch 84 is actuated to the "power on" position and power is received by the logic circuit of FIG. 16.

Symbols S2 and S3 respectively represent the selection of "mode 1" or "mode 2", as determined by the position of rocker switch 85.

The symbol S4 in the display D consists of crossed mining hammers and represents the analysis of a "natural" gemstone. In addition, the symbol S4 includes a gemstone that flashes intermittently to better evidence the analysis of a "natural" gemstone.

Symbol S5 on the display D comprises a balance beam symbol and indicates an abnormal condition to the user, one of which is a gem specimen that is not within the species corresponding to the selected mode.

Symbol S6 on the display D is a mortar and pestle, representing a laboratory or synthetic process for the gem specimen under analysis.

The arbitrary, unitless number N comprises three seven-segment decimal digits ranging from 0-999 and constitutes a numerical readout that is directly proportional to the magnitude of the analog signal from the photocell detector 71. The arbitrary numerical range for "natural" gem specimens in the preferred embodiment of the inventive apparatus is 10-60. The "transition" range runs from 61-90, and the range for "synthetic" specimens runs from 91-999.

Figure 18A:
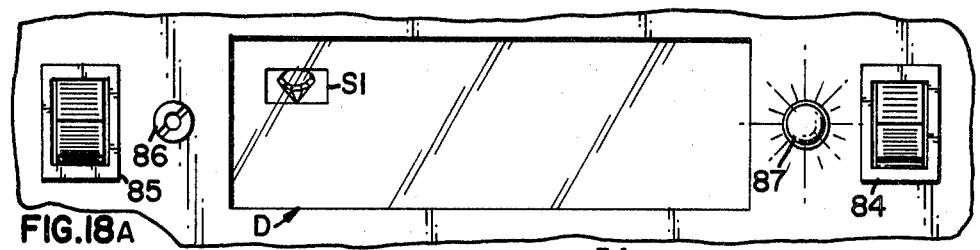
FIGS. 18A–18F are individual representations of the control and display panel of the apparatus showing various output displays.

FIGS. 18A-18F disclose the entire inclined section 13b, including the rocker switches 84, 85, the calibration potentiometer 86, the "source on " LED 87, and the display D of the liquid crystal display 96. With reference to FIG. 18A, the presence of the single symbol S1 indicates that the rocker switch 84 is actuated to the "power on" position and power is received by the logic circuit of FIG. 16. Also, the LED 87 is shown to be in the "on" position, which means that the discharge source lamp 21 is properly operating in a stable condition. The LED 87 is shown in the "discharge source on" condition in all of the FIGS. 18A-18F.

Figure 18B:
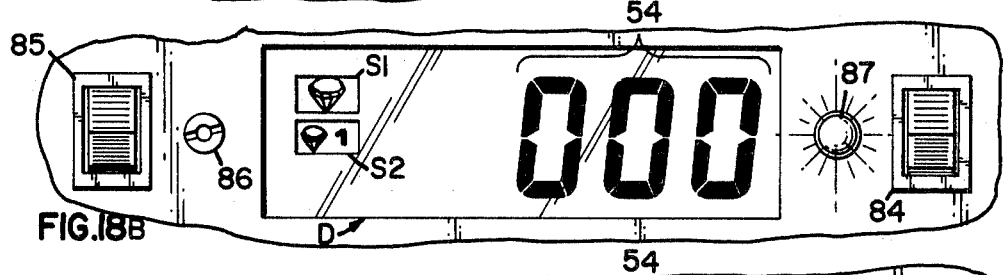
Figure 18C:
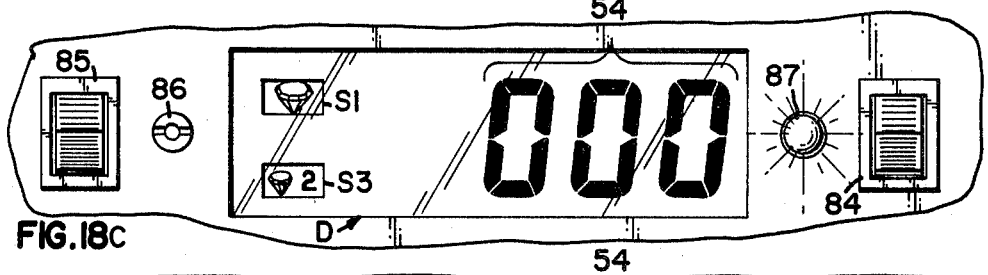

With reference to FIG. 18B, the symbol S2 represents selection of "mode 1" as determined by the position of rocker switch 85. In FIG. 18C, the symbol S3 is indicative of the selection of "mode 2" by the rocker switch 85. The selection of "mode 1" in the preferred embodiment is for analysis of the ruby species, and "mode 2" is chosen to analyze the emerald species.

In both FIGS. 18B and 18C, the decimal number N is "000", which indicates occlusion of the test aperture 61a or some other obstruction which precludes radiation from reaching the photocell 71, or an open test aperture 61a (e.g., absence of a gem specimen).

Figure 18D:
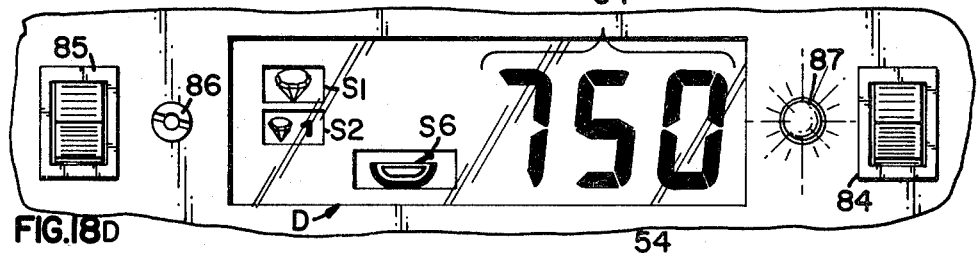

With reference to FIG. 18D, the display D includes the symbol S1 indicating "logic on", the symbol S2 showing selection of "mode 1" and the symbol S6, representing a laboratory or synthetic process for the gem specimen under analysis. The digital readout N is 750, which falls within the synthetic range as described above.

Figure 18E:
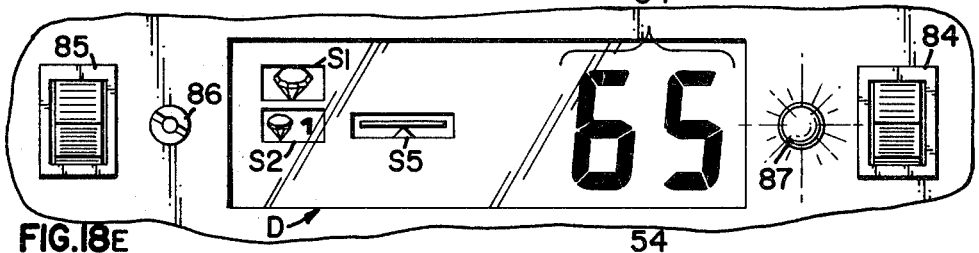

In FIG. 18E, symbol S1 displays "logic on" and symbol S2 is again selected for ruby analysis. The balance beam symbol S5 indicates an abnormal condition to the user, as does the digital readout N, which has a value of 65. This falls within the "transition" range as described above, and indicates to the user one of several possibilities, including improper operation or analysis of a gem specimen that is not a ruby.

Figure 18F:
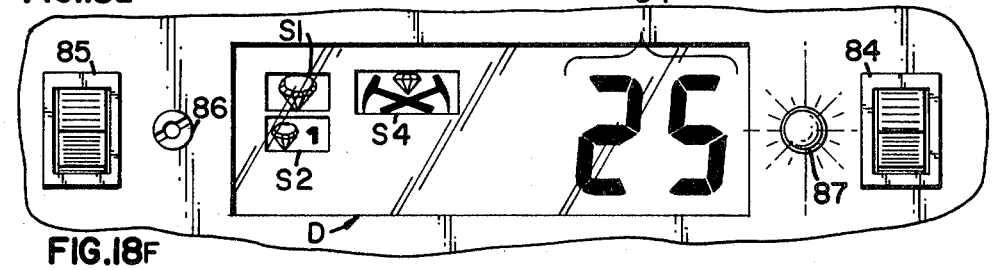

In FIG. 18F, symbol S1 shows a "logic on" status, symbol S2 shows that "mode 1" has again been selected for ruby analysis, and the symbol S4 indicates analysis of a "natural" gemstone. The additional gemstone symbol flashes to further evidence this analysis. The digital readout N is at 25, which falls within the arbitrary range for "natural" gem specimens as set forth above.

The operation of the detector, analog to digital converter, comparator, logic, and display circuits will now be explained. Referring to FIG. 14, radiation falling on photocell 71 produces a corresponding voltage on conductor 119. The voltage on conductor 119 is fed through conductor 118 to the comparator circuits of FIG. 15 and further applied to the input (pin 31) of analog to digital converter 92 through resistor 121. Converter 92 periodically digitizes the analog current appearing at its input through resistor 121 and outputs through a plurality of conductors 93, the signals of which are encoded for driving the three seven-segment displays of display 96a. Accordingly, a three-place decimal number directly proportional to the radiation falling on photocell 71 is displayed.

Referring to FIG. 15, conductor 118 carries the generated analog voltage to one input of each of comparators 128, 129, 130 and 131. As described above, comparators 128 and 129 work in cooperation to define a "window" in the analog voltage range associated with the particular family of gems under test. Therefore, the analog voltage associated with any particular gem under test may fall in one of three ranges: (1) below the lower limit of the window; (2) about the upper limit of the window; or (3) inside the window range. When operational amplifiers 128 and 129 are switched through relays 139 and 140 to level shifting inverter 142, outputs 145 and 146 will produce a two bit digital code corresponding to the position of the analog voltage on conductor 118 with respect to the window defined by potentiometers 124 and 125 of network 123. If, for example, the voltage appearing on conductor 118 is below the window, the output of comparator 128 will be low and a corresponding logic 1 voltage will appear on conductor 145, while the output of operational amplifier 129 will be high with a corresponding logic 0 voltage on output 146. If the voltage on conductor 118 is within the window, the outputs of both comparators 128 and 129 will be high with corresponding logic 0 voltages on conductors 145 and 146. Finally, if the voltage on conductor 118 is above the window the output of operational amplifier 129 will be low with a corresponding logic 1 voltage on output 146. The output of operational amplifier 128 will be high with a corresponding logic 0 voltage on conductor 145. In this manner, one of the three logic conditions 1-0, 0-0, or 0-1 will be present on conductors 145 and 146 of level shifting inverter 142 when a gem is under test.

Comparators 130 and 131 operate in the same manner only with a different window defined through potentiometers 126 and 127 for a different family of gems. The outputs generated on conductors 147 and 148 indicate the position of rocker switch 85, and relays 139 and 140. Depending on the position of rocker switch 85, one of outputs 147 and 148 is activated, with the other output in a complementary state.

The comparator network defined by comparators 136, 137 and 138 and connected to level shifting inverter network 151 is also connected to conductor 118. Like comparators 128 and 129 or 130 and 131, and as described above comparators 137 and 138 also define a window voltage range. Comparator 136 defines a lower limit voltage for detecting occlusions in the gem test aperture 61a. Accordingly, whenever the voltage appearing on conductor 118 is below the lower limit voltage, the output of operational amplifier 136 is low producing a corresponding logic 1 output on conductor 152. Similarly, a voltage on conductor 118 falling within the window defined by operational amplifiers 137 and 138 will produce a logic 1-1 at conductors 153 and 154. The window voltage is carefully defined to closely frame the voltage corresponding to an open test aperture 61a that is where the radiation falling on photocell 71 is direct from lamp 21.

In the preferred embodiment, the low reference voltage for the operational amplifier 136 is the lowest reference voltage, and may be on the order of 1 millivolt. The reference voltage for operational amplifier 128 is on the order of 6 millivolts in the preferred embodiment, and the reference voltage for operational amplifier 129 is 9 millivolts. Thus, any analog signal from the photocell 71 which falls between 1 millivolt and 6 millivolts falls in the "natural" gem range, subject to the exception defined below. Any analog signal from photocell 71 that exceeds 9 millivolts is in the "synthetic" range. Any analog signal below 1 millivolt is treated as a spurious signal and is processed in a manner that precludes a readout.

The "window voltage range" defined by the operational amplifiers 137 and 138 is between 3.5 millivolts and 4.5 millivolts in the preferred embodiment, and constitutes the exception mentioned immediately above. It will be appreciated that this narrow range falls within the range indicative of "natural" gems. However, this range is chosen based on the fact that natural gemstones such as rubies will not produce an analog voltage in this particular range (given the other parameters of the electronic circuitry). The reason for this is that some natural gemstones within a particular species will undergo internal excitation (e.g., fluorescence), whereas others do not. Thus, with the parameters of the preferred embodiment, a natural ruby which does not emit fluorescence will produce an analog voltage in the range of 1 to 3.5 millivolts. A natural ruby that emits fluorescence will produce an analog signal between the range of 4.5 millivolts and 9 millivolts. It has been found as a practical matter that natural rubies will not produce a signal between 3.5 millivolts and 4.5 millivolts in the preferred embodiment. However, the electronic circuitry is designed so that radiation exposed to the photocell 71 through an open test aperture 61a will fall within the range of 3.5–4.5 millivolts.

It will be appreciated that the millivolts reference values described above are mentioned for guidance only, and are chosen in the preferred embodiment only for particular circuit parameters and gem species. These voltage levels may be adjusted for the same or different species to produce different reference values, which would in turn give rise to different unitless, arbitrary decimal numbers and different ranges of operation.

The interpretation of the logic signals generated on outputs 145–148 and 152–154 is preformed by the logic circuitry shown in FIG. 16. Additionally, the logic of FIG. 16 gates the applied signals to produce the square waves necessary for driving the symbols of liquid crystal display 96b.

In the operation of the liquid crystal display 96b a square wave is generated on conductor 116b by analog to digital converter 92. The square wave is input to one input of each of the exclusive-or gates 162a, 162b, 162c, 162d, 162e and 162h. It is further input of the back plane connection of LCD 96b. The outputs of gates 162b, 162c, 162d, 162e and 162h are connected to the various liquid crystal symbols 51–53 and 55–57 which represent "logic on" "mode 1", "mode 2", "synthetic", "transition" and "natural". The "gem" symbol associated with the "natural gem" symbol S1 is gated through oscillator 162i so that it appears flashing on the display. When a natural gem is detected by comparator logic 94 a logic 1 or high voltage appears on conductor 145. It is applied to one input of each and-gate 162j and 162k. The signal propagates through each of these gates and is applied to the respective gates 162L and 162a. The application of a logic 1 voltage to the upper input of gate 162a causes its output square wave to shift out of phase with the square wave appearing on conductor 116b and consequently excites the "crossed mining hammer" portion of symbol S4 on LCD 96b. The flashing gem portion of the symbol S4 is driven through gates 162m, 162L and gate 162j.

As mentioned above, the output of operational amplifiers 136, 137 and 138 provide spurious condition information to the logic. Outputs 152, 153 and 154 from level shifting inverter 151 are input to the corresponding conductors shown in the lower lefthand corner of FIG. 16. In the case where the voltage level appearing on conductor 118 is less than the defined lower limit, a logic 1 voltage appears on conductor 152 and is passed through or-gate 162n and inverter 162o, disabling and-gates 162k and 162j. The gates thus disabled, neither symbol associated with the natural gem appears on LCD 96b. Further, when the voltage on conductor 118 falls within the window defined by comparators 137 and 138 a logic 1 condition appears on conductors 153 and 154 and thus produces a logic 1 output on and-gate 162p, consequently disabling the "natural" symbols through or-gate 162n in a similar fashion.

When the gem under test falls in the "transistion" window the inputs on conductors 145 and 146 are both logic 0's. Consequently, neither square wave output from gates 162a or 162b is phase shifted, and their corresponding symbols are not energized. Instead, the logic 0 signals appearing on conductors 145 and 146 are fed into or-gate 162f to produce a 0 output voltage for input to the upper input of or gate 162g. Given a logic 0 on the output of or-gate 162n, a logic 1 appears on the output of gate 162g and is input to the lower input of exclusive or-gate 162h. As a result, the square wave output of gate 162h is phase shifted with respect to the back plane square wave of 116b and the "transition" symbol is energized on LCD 96b.

When the gem under test falls in the "synthetic" range, comparator circuits 94 produce a logic 0-1 code on the respective conductors 145 and 146. Thus, the output square wave of exclusive or-gate 162b is phase shifted and delivered through conductor 156 to energize the "synthetic" symbol on LCD 96b. The "logic on" symbol is driven through gate 162e, which is driven by inverter 162q. As pointed out earlier, the input to gate 162q is derived from the collector transistor 115 (FIG. 14). The "mode 1" and "mode 2" symbols are driven by the respective outputs of gates 162c and 162d through the respective conductors 157 and 158. The phase shifting inputs to gates 162c and 162d are derived from conductors 147 and 148 which are connected to level shifting inverter 142. Depending on the mode in which the apparatus is operating, a logic 1 condition will appear on one of the two conductors 147 and 148 and consequently shift the corresponding square wave to excite the respective mode symbol.

In understanding operation of the apparatus 11, it must also be emphasized that the discharge source 21 and photocell detector 71 are uniquely related to each other and to the species of gems to be analyzed. More specifically, and as pointed out above, the quartz tube mercury discharge lamp 21 emits radiation in a broad spectrum of electromagnetic energy, the wave length of which ranges from approximately 1800 Angstoms in the far-ultraviolet region at the low end through the visible region and into the near-infrared region. This particular lamp peaks at several individual wavelengths, the principal of which is 2550 Angstoms.

Both natural and synthetic rubies undergo internal excitation or fluorescence which produces a frequency shift, resulting in the emission of electromagnetic energy at approximately 6500 Angstroms. The photodetector 71 is specifically chosen because it senses electromagnetic energy in the narrow region around 6500 Angstroms.

It is the total interaction of the electromagnetic energy from the lamp 21 with the gem specimen which permits quantification in discrete ranges. This interaction includes the transmission of electromagnetic energy through the gem specimen, which is the complement of absorption. Energy is transmitted through the gem and emits from the gem at the same wavelength at which it enters. Only the intensity, as evidenced by the degree of absorption, is affected.

Interaction also includes internal reflectance, which is largely a function of atomic imperfections and includes (e.g., random iron molecules or structural imperfections in natural ruby). The internal reflectance alters only the intensity of electromagnetic energy emitted from the gem, and not is frequency and wavelength.

Lastly, interaction of the electromagnetic source with the gem involves internal excitation, a principal form of which is fluorescence. As pointed out above, this causes a frequency shift, and the resulting electromagnetic energy emitted from the gem falls within a spectrum of wavelength entirely different than the excitation wavelength.

The total interaction gives rise to output radiation from the gem which represents a highly complex wave form if the entire spectrum is taken into consideration. However, the red and blue glass filters 68, 69 mask this spectrum, focusing on the specific region of radiation at around 6500 Angstroms. This takes advantage of the frequency shift from the 2500 angstrom peak caused by fluorescence, as discussed above. However, the photocell detector 71 not only measures the intensity of electromagnetic energy caused by fluorescence, but also the cumulative effect produced by transmitted, nonabsorbed electromagnetic energy in the detected range as well as the radiation produced by internal reflection. It is to be emphasized that it is the cumulative effect of interaction of lamp radiation with the gem that is sensed by the detector in the range of about 6500 Angstroms, such cumulative effect being sensed as intensity of the electromagnetic energy in the detected 6500 Angstrom range.

Operation of the apparatus 11 from the standpoint of the user is simple and efficient. The unit must be connected to a source of 110 volt or 220 volt power with internal switch 34 first actuated to the corresponding voltage position. The apparatus 11 may then be turned on through use of the rocker switch 84. When the lamp 21 reaches a stabilized voltage level of operation, the light emitting diode 87 on the inclined panel 13b will light up, indicating that the unit is ready for use.

The mode is then selected with rocker switch 85. Assuming that "mode 1" is chosen, the drawer 19 is opened by use of the latch 64, and the gem specimen in question is placed on the specimen holder 61 in a position to completely overlie the test aperture 61a. The size of aperture 61a is chosen to be smaller than the vast majority of potential gem specimens, thus insuring that all of the radiation from the gem will be the product of its interaction with the source of radiation from lamp 21.

With the gem specimen properly placed, the drawer 19 is closed and the latch 64 actuated to lock the drawer. As discussed above, this causes all of the apertures between the lamp 21 and photocell 71 to be in registration, permitting interaction to occur between the specimen and the electromagnetic energy radiated by lamp 21.

As an instantaneous result, an analog signal is generated by the photocell 71 which is directly proportional to the intensity of electromagnetic energy to which the photocell 71 is exposed. As described above, this analog signal can be processed by the electronic circuitry to quickly and automatically provide a readout as to whether the gem is natural or synthetic, as well as an indication of its quality as evidenced by the numerical digital readout. If an occlusion of the test aperture 61a appears, or if the aperture 61a is open for any reason, the numerical digital readout is "000". If the gem specimen analyzed is not within the species expected, the "balance beam" symbol S6 will appear and the numerical digital readout will fall in the "transition" range.

It is advisable to calibrate the apparatus 11 periodically to compensate for operational shifts such as aging of the electronic or electrical components. This is easily accomplished by removing the loosely held specimen holder 61 from the drawer 19 and replacing it with the specimen holder 89 and calibration specimen 88, which has a known value expressed as a three digit number. With the calibration specimen in place and the drawer 19 closed, the calibration potentiometer 86 is adjusted until the numerical digital readout symbol S4 corresponds to the known digital number of the calibration specimen 88. The apparatus 11 is then calibrated for further use.

What is claimed is:

1. Apparatus for analyzing gem specimens, comprising:

housing means;

a source of radiated energy carried by the housing means capable of emitting electromagnetic radiation over a wide spectrum of wavelengths of varying intensity;

holder means for supporting a gem specimen in a predetermined position relative to the source of radiated energy, the holder means being opaque to said radiated energy and having an aperture formed therethrough in which the gem specimen is disposed, and through which at least part of the gem specimen is exposed to said radiated energy;

the holder means and the source of radiated energy being constructed and arranged so that the radiated energy interacts with said gem specimen, causing it as a result to emit radiated energy over a wide spectrum of wavelengths of varying intensity;

detector means carried by the housing means in a position in which it is exposed to the energy emitted by said gem specimen and constructed to detect the intensity of energy emitted by said gem specimen over a spectrum of wavelengths that is narrow relative to the spectrum of wavelengths emitted by said gem specimen, said narrow spectrum being chosen as a function of known response of a particular species of gem to radiated energy;

signal means associated with the detector means for generating an electric signal representative of the intensity of energy emitted by the gem specimen and detected by the detector means;

and readout means associated with the signal means for providing a readout in response to said electric signal that is representative of the nature of the gem specimen.

2. The apparatus defined by claim 1, wherein the housing means includes means defining an optically sealed chamber.

3. The apparatus defined by claim 2, wherein the holder means is disposed in the optically sealed chamber.

4. The apparatus defined by claim 3, wherein the chamber defining means and holder means are movable relative to the source of radiated energy and the detector means between a first position in which the holder means is disposed in registration with said source and detector means, and a second position in which the holder means is accessible externally of the apparatus.

5. The apparatus defined by claim 4, which further comprises shutter means for establishing communication between the source of radiated energy and detector means with the chamber defining means in said first position, and for blocking communication between the source of radiated energy and detector means with the chamber defining means in said second position.

6. The apparatus defined by claim 5, wherein the optically sealed chamber comprises a drawer.

7. The apparatus defined by claim 6, which further comprises latching means for latching the drawer in said first position.

8. The apparatus defined by claim 7, wherein the shutter means comprises means associated with the drawer for defining at least two apertures which are disposed in registration with the drawer in the first position and out of registration with the drawer in the second position.

9. The apparatus defined by claim 1, wherein the holder means comprises:
a first support member formed from material that is opaque to the energy radiated from said source, said aperture being disposed in the first support member;
and a second support member underlying the first member and said aperture, the second support member being formed from material that is transparent to the energy radiated from said source.

10. The apparatus defined by claim 1, wherein the source of radiated energy and the detector means are disposed on opposite sides of the holder means.

11. The apparatus defined by claim 1, wherein the signal means is constructed and arranged to generate a first signal if the intensity of energy emitted by the specimen is below a first predetermined level, and a second signal if said intensity is above a second predetermined level.

12. The apparatus defined by claim 11, wherein the readout means comprises first and second readouts respectively actuated by the first and second signals of the signal means.

13. The apparatus defined by claim 1, wherein the signal means is constructed and arranged to generate a first signal if the intensity of energy emitted by the specimen is below a first predetermined level, a second signal if said intensity is above a second predetermined level, and a third signal if said intensity is between the first and second predetermined levels.

14. The apparatus defined by claim 13, wherein the readout means comprises first, second and third readouts respectively actuated by the first, second and third signals of the signal means.

15. The apparatus defined by claim 1, wherein the signal means is constructed and arranged to generate an analog signal representative of the intensity of said emitted energy.

16. The apparatus defined by claim 15, wherein the readout means provides a readout corresponding to said analog signal.

17. The apparatus defined by claim 16, wherein said readout is digital.

18. The apparatus defined by claim 1, wherein:
the detector means produces an analog output that varies as a direct function of the intensity of energy emitted from the specimen;
and the signal means comprises electronic circuit means
for comparing said analog output with first and second reference values and generating a first signal if the analog output is below the first reference value, a second signal if the analog output is above the second reference value, and a third signal if the analog output is between the first and second reference values;
and for generating a fourth signal which is analog in nature and directly proportional to the analog output.

19. The apparatus defined by claim 18, wherein the readout means provides first, second, third and fourth readouts corresponding to the first, second, third and fourth signals.

20. The apparatus defined by claim 19, wherein:
the first readout is indicative of a natural gem specimen;
the second readout is indicative of a synthetic gem specimen;
the third readout is indicative of a gem of indeterminate nature;
and the fourth readout is numerically digital.

21. The apparatus defined by claim 20, wherein:
the first readout means comprises a representation of crossed mining hammers;
the second readout means comprises a representation of a mortar and pestle; and
the third readout means comprises a representation of a balance beam.

22. The apparatus defined by claim 18, wherein said electronic circuit means compares the analog output with a third reference value less than the first reference value and generates a fifth signal if the analog output is below said third reference value.

23. The apparatus defined by claim 22, wherein the readout means provides a fifth readout in response to the fifth signal indicative of a first abnormal condition.

24. The apparatus defined by claim 23, wherein the electronic circuit means compares the analog output with fourth and fifth reference values both of which are less than the first reference value and greater than the third reference value, said electronic circuit means generating a sixth signal if the analog output falls between the fourth and fifth reference values.

25. The apparatus defined by claim 24, wherein the readout means provides a sixth readout in response to the sixth signal indicative of a second abnormal condition.

26. The apparatus defined by claim 25, wherein:
the fifth readout is indicative of a condition in which the detector means is blocked from exposure to radiated energy;
and the sixth readout is indicative of a condition in which there is no specimen present on the holder means.

27. The apparatus defined by claim 26, wherein the readout means comprises a numerical digital display, and each of the fifth and sixth readouts comprises a "0" readout on said numerical digital display.

28. The apparatus defined by claim 18, which further comprises means for detecting operative and inoperative states of the electronic circuit means, and means for annunciating the state of operation of the electronic circuit means.

29. The apparatus defined by claim 28, wherein the annunciating means comprises a representation on said readout means of a gem.

30. The apparatus defined by claim 18, wherein:
the first and second reference values comprise a first pair and correspond to a particular gem species, and the electronic circuit means is further constructed and arranged to compare the analog signal with at least one additional pair of reference values corresponding to a different gem species;
and further comprising switching means for selecting operation with either the first or second pairs of reference values.

31. The apparatus defined by claim 30, wherein the readout means, signal means and switching means cooperate to display a "mode 1" readout corresponding to selection of said first pair of reference values, and a "mode 2" readout corresponding to selection of said second pair of reference values.

32. The apparatus defined by claim 1, which further comprises means for detecting operative and inoperative states of the source of radiated energy, and means for annunciating the state of operation of the source of radiated energy.

33. The apparatus defined by claim 32, wherein the annunciating means comprises a light emitting diode.

34. The apparatus defined by claim 1, which further comprises filter means associated with the detector means for blocking the detector means from energy emitted from the specimen except in said narrow spectrum.

35. The apparatus defined by claim 34, wherein the filter means comprises at least one optical filter disposed between the holder means and the detector means.

36. The apparatus defined by claim 34, wherein the filter means comprises first and second optical glass filters sequentially disposed between the holder means and the detector means, the first filter being disposed nearest the holder means and being constructed to filter all radiation except in the visible red range, and the second filter being constructed to filter all radiation except in the visible blue range.

37. The apparatus defined by claim 1, wherein the source of radiated energy comprises an unfiltered quartz mercury discharge lamp and the detector means comprises a photocell.

38. The combination as set forth in claim 1 in which the apparatus is constructed to be electrically powered at a predetermined voltage level, and further comprising conversion means for enabling usage of the apparatus at at least one ohter voltage level.

39. Apparatus for analyzing gem specimens comprising:
energy radiating means for radiating electromagnetic energy over a first wide spectrum of wavelengths of varying intensity,
holder means for holding a gem specimen relative to the energy radiating means so that radiated energy interacts with the gem specimen, causing it to emit radiated energy as the result of said interaction over a second wide spectrum of wavelengths of varying intensity;
detector means disposed in a position in which it is exposed to said second spectrum of radiated energy for sensing the integrated response of the specimen resulting from said interaction over a spectrum that is narrow relative to the second spectrum, said narrow spectrum being chosen as a function of known response of a particular species of gem to radiated energy;
signal means for generating a signal representative of the integrated response as sensed by the detector means;
and readout means associated with the signal means for providing a readout in response to said signal that is representative of the nature of the gem specimen.

40. The apparatus defined by claim 39, which further comprises filter means for blocking the detector means from energy emitted from the specimen except in said portion of the second spectrum.

41. The apparatus defined by claim 39, wherein said signal is analog and the readout means in constructed and arranged to display a numerical digital readout corresponding to the magnitude of said analog signal.

42. The apparatus defined by claim 39 or 41, wherein the signal means is constructed and arranged for processing said signal and generating first and second mutually exclusive signals respectively indicating that the gem specimen is "natural" or "synthetic".

43. The apparatus defined by claim 42, wherein the readout means comprises "natural" and "synthetic" symbols that are respectively displayed in response to said first and second signals.

44. A method of analyzing gem specimens comprising:
causing electromagnetic energy to be radiated over a first wide spectrum of wavelengths of varying intensity;
disposing a gem specimen relative to the first spectrum of electromagnetic energy so that the radiated energy interacts with the gem specimen, causing it to emit radiated energy as the result of said interaction over a second wide spectrum of wavelengths of varying intensity;
sensing the integrated response to the specimen resulting from said interaction over a spectrum that is narrow relative to the second spectrum, said narrow spectrum being chosen as a function of known response of a particular species of gem to radiated energy;
generating a signal respresentative of the integrated response as sensed; and
providing a readout in response to said signal that is representative of the nature of the gem specimen.

45. The method defined by claim 44, wherein the sensed portion of said second spectrum comprises a spectrum that is narrow relative to the second spectrum, said narrow spectrum being chosen as a function of known response of a particular species of gem to radiated energy.

46. Apparatus for distinguishing between natural and synthetic gem specimens of the same gem type, comprising:
housing means;
a source of radiated energy carried by the housing means capable of emitting electromagnetic radiation over a wide spectrum of wavelengths of varying intensity;

holder means for supporting a gem specimen in a predetermined position relative to the source of radiated energy, the holder means being opaque to said radiated energy and having an aperture formed therethrough in which the gem specimen is disposed, and through which at least part of the gem specimen is exposed to said radiated energy;

the holder means and the source of radiated energy being constructed and arranged so that the radiated energy interacts with said gem specimen, causing it as a result to emit radiated energy over a wide spectrum of wavelengths of varying intensity;

detector means carried by the housing means in a position in which it is exposed to the energy emitted by said gem specimen and constructed to detect the intensity of energy emitted by said gem specimen over a spectrum of wavelengths that is narrow relative to the spectrum of wavelengths emitted by said gem specimen, said narrow spectrum being chosen based on the known difference in response to radiated energy between natural and synthetic specimens of the same gem type;

signal means associated with the detector means for generating an electric signal representative of the intensity of energy emitted by the gem specimen and detected by the detector means;

and readout means associated with the signal means for providing a readout in response to said electric signal that indicates whether the gem specimen is natural or synthetic.

* * * * *

UNITED STATES PATENT AND TRADEMARK OFFICE
CERTIFICATE OF CORRECTION

PATENT NO. : 4,394,580
DATED : July 19, 1983
INVENTOR(S) : Peter J. Gielisse

It is certified that error appears in the above-identified patent and that said Letters Patent are hereby corrected as shown below:

Column 10, line 39, delete "mechaical", and insert therefor --mechanical--.

Column 11, line 29, delete "E3", and insert therefor --E2--.

Column 18, line 62, delete "Angstoms", and insert therefor --Angstroms--.

Column 18, line 66, delete "Angstoms" and insert therefor --Angstroms--.

Column 19, line 20, delete "is" and insert therefor --its--

Column 23, line 60, delete "at".

Column 23, line 60, delete "ohter" and insert therefor --other--.

Column 24, line 24, delete "in" and insert therefor --is--.

Signed and Sealed this

Seventeenth Day of April 1984

[SEAL]

Attest:

GERALD J. MOSSINGHOFF

*Attesting Officer*   *Commissioner of Patents and Trademarks*